United States Patent
Peyman et al.

(10) Patent No.: US 6,280,471 B1
(45) Date of Patent: Aug. 28, 2001

(54) GLARE-FREE INTRAOCULAR LENS AND METHOD FOR USING THE SAME

(76) Inventors: Gholam A. Peyman, 8654 Ponchartrain Blvd., New Orleans, LA (US) 70124; Jeffrey E. Koziol, 1211 S. Arlington Heights Rd., Arlington Heights, IL (US) 60005

( * ) Notice: Subject to any disclaimer, the term of this patent is extended or adjusted under 35 U.S.C. 154(b) by 0 days.

(21) Appl. No.: 09/553,846

(22) Filed: Apr. 20, 2000

Related U.S. Application Data

(63) Continuation-in-part of application No. 09/397,036, filed on Sep. 16, 1999.

(51) Int. Cl.⁷ .................................................... A61F 2/16
(52) U.S. Cl. ....................... 623/6.17; 623/6.14; 623/6.32; 623/6.34
(58) Field of Search .................. 623/6.11, 6.14, 623/6.17, 6.32, 6.34

(56) References Cited

U.S. PATENT DOCUMENTS

| | | | |
|---|---|---|---|
| Re. 34,251 | * 5/1993 | Achatz et al. ........................... | 623/6 |
| 4,676,791 | * 6/1987 | LeMaster et al. .................. | 623/6.17 |
| 4,678,469 | * 7/1987 | Kelman ............................... | 623/6.17 |
| 4,743,254 | * 5/1988 | Davenport .............................. | 623/6 |
| 4,769,033 | * 9/1988 | Nordan ................................... | 623/6 |
| 4,813,955 | * 3/1989 | Achatz et al. .......................... | 623/6 |
| 4,816,032 | * 3/1989 | Hetland .............................. | 623/6.14 |
| 4,906,246 | * 3/1990 | Grendahl ........................... | 623/6.28 |
| 4,917,681 | * 4/1990 | Nordan ................................... | 623/6 |
| 4,919,663 | * 4/1990 | Grendahl ........................... | 623/6.28 |
| 5,019,099 | * 5/1991 | Nordan ................................... | 623/6 |
| 5,074,877 | * 12/1991 | Nordan ................................... | 623/6 |
| 5,120,120 | * 6/1992 | Cohen .................................. | 351/161 |
| 5,152,788 | * 10/1992 | Isaacson et al. .................... | 623/6.34 |
| 5,236,452 | * 8/1993 | Nordan ................................... | 623/6 |
| 5,326,348 | * 7/1994 | Nordan ................................... | 623/6 |
| 5,549,670 | * 8/1996 | Young et al. ........................ | 623/6.17 |
| 5,578,080 | * 11/1996 | McDonald .......................... | 623/6.17 |
| 5,682,223 | * 10/1997 | Menezes et al. ...................... | 351/161 |
| 5,684,560 | * 11/1997 | Roffman et al. ...................... | 351/160 |
| 5,702,440 | * 12/1997 | Portney .................................. | 623/5 |
| 5,715,031 | * 2/1998 | Roffman et al. ...................... | 351/161 |
| 5,755,786 | * 5/1998 | Woffinden et al. ................... | 623/15 |

OTHER PUBLICATIONS

"Ocular Surgery News", Jan. 1, 1999, pp. 6–10, p. 12.*

* cited by examiner

*Primary Examiner*—Dinh X. Nguyen
(74) *Attorney, Agent, or Firm*—Roylance, Abrams, Berdo & Goodman, L.L.P.

(57) ABSTRACT

An IOL that is free of glare and the halo effect associated with conventional IOLs and a method for using the same is provided. The IOL is adapted for implantation into an eye, in place of or in addition to the natural lens of the eye, to adjust a refractive power of an eye. The IOL includes at least one lens portion and a light-absorbing material. The lens portion has first and second surfaces and a perimeter connecting the first and second surfaces which extends entirely about the lens portion. The first and second surfaces can have any suitable shape to provide the lens portion with a suitable refractive power. The light-absorbing material is disposed to absorb light propagating in a direction towards the perimeter to thus eliminate glare and the halo effect caused by such light. One or more haptics, which include a light absorbing material, can be attached to the lens portion for mounting the IOL in the eye. The light absorbing material of the haptics absorbs light impinging on the haptics to further eliminate glare and the halo effect. The lens portion may have at least one opening or hole cut in the lens for allowing aqueous fluid to pass from behind the iris through the lens and into the anterior chamber.

18 Claims, 34 Drawing Sheets

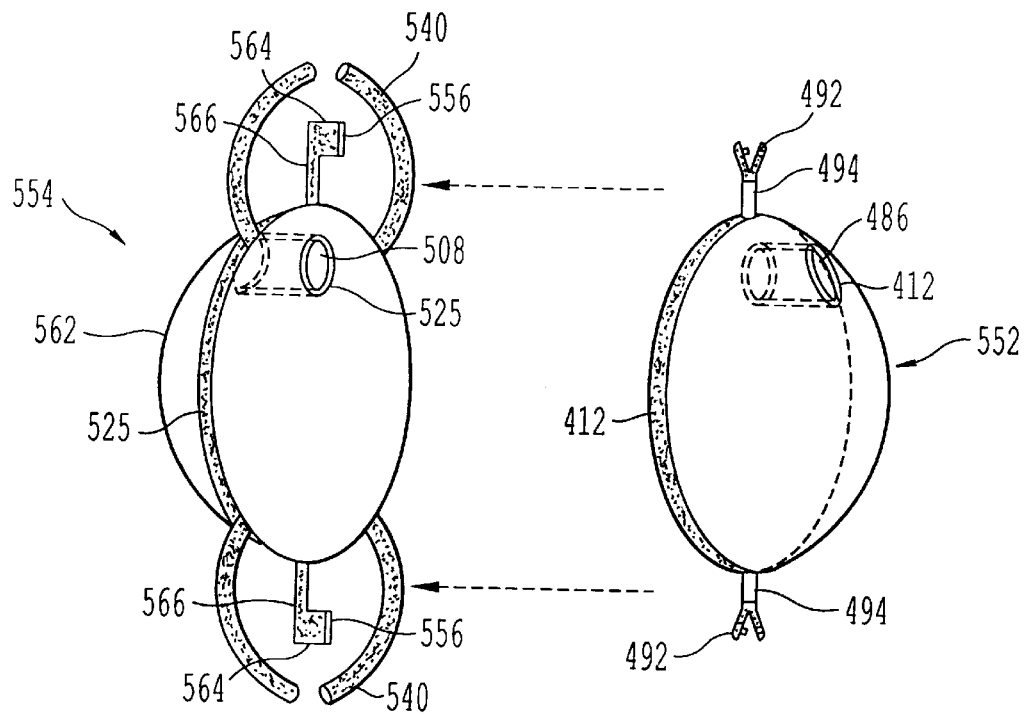
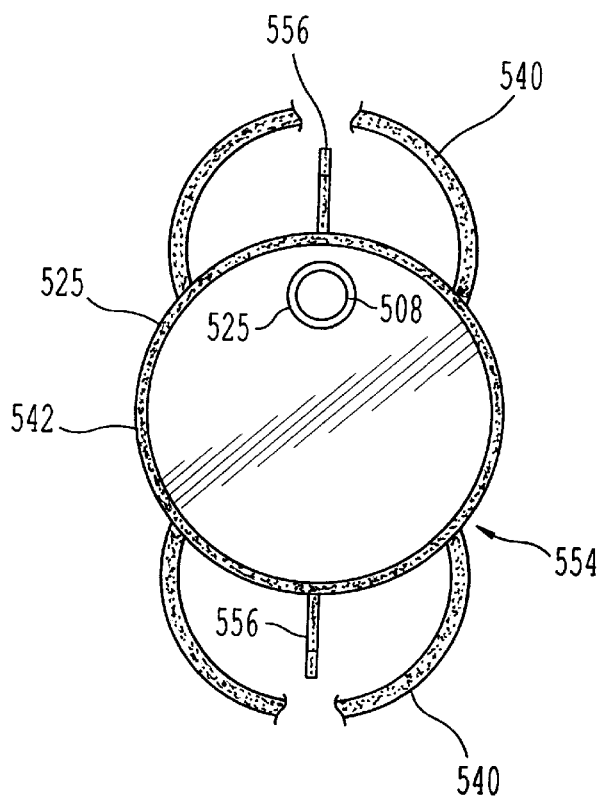
FIG. 60
FIG. 61

GLARE-FREE INTRAOCULAR LENS AND METHOD FOR USING THE SAME

CROSS-REFERENCE TO RELATED APPLICATION

Related subject matter is disclosed in copending U.S. Patent Application of Gholam A. Peyman and Jeffrey E. Koziol entitled "Lens Conversion System for Teledioptic or Diffractive Configurations", U.S. Ser. No. 09/178,739, filed on Oct. 27, 1998, the entire contents of which is incorporated herein by reference.

This application is a continuation-in-part of application Ser. No. 09/397,036 filed Sep. 16, 1999. The entire contents of which are incorporated herein by reference.

BACKGROUND OF THE INVENTION

1. Field of the Invention:

The present invention relates to a glare-free single focal or multifocal intraocular lens and method for using the same. More specifically the present invention relates to an intraocular lens having one or more focusing areas and a light-absorbing material for absorbing undesired light rays to minimize glare experienced by the eye of the patient in which the intraocular lens is implanted.

2. Description of the Related Art

An intraocular lens (IOL) is a transparent lens made of a synthetic or other suitable material for implantation into an eye in place of or in addition to the natural lens of the eye to correct the vision of the eye. Many different types of IOLs exist for correcting various types of vision disorders. For example, an IOL can be formed in the same shape of a natural lens of an eye that has been damaged, and can be inserted into that eye in place of the natural lens.

Alternatively, in an eye suffering from myopia, hyperopia or astigmatism, an IOL can be formed to have a bi-convex, bi-concave, plano-concave, plano-convex, concave-convex, or any other shape suitable which provides the IOL with the appropriate focusing power to correct for the error in focusing power of the eye that is causing the vision disorder. The suitably shaped IOL can be implanted into the eye in place of or in addition to the natural lens to thus correct the focusing power of the eye and eliminate the vision disorder.

Although existing IOLs are somewhat suitable for correcting visions disorders, they typically cause the eye to experience an undesirable side effect commonly referred to as a "halo effect", which is a ring of light that the person will see in the eye having the implanted IOL. A halo effect is caused due to light entering or being refracted by the IOL at certain angles which creates a glare that is sensed by the retina of the eye and thus experienced by the person. Also, reflection of light off of haptics used for mounting the IOL in the eye can also increase the intensity of the halo effect.

Although the severity of the halo effect can vary depending on the shape of the IOL and the amount of direct and ambient light being received by the eye, the halo effect can cause the patient much annoyance. Also, in certain instances, the halo effect can also adversely affect the patient's ability to read, drive a car and perform other routine activities requiring acute vision. The halo effect is discussed in more detail in an article entitled "Surgeon has insider's view of the Array multifocal IOL," Ocular Surgery News, pp. 6–12, Jan. 1, 1999.

To reduce the halo effect in IOLs having multiple focusing powers, these types of IOLs can include a darkened material at the interface between the different refractive power sections of the IOL. Examples of these types of IOLs are disclosed in U.S. Pat. Nos. 5,326,348, 5,236,452, 5,074,877, 5,019,099, 4,917,681 and 4,769,033, all to Nordan, as well as in U.S. Pat. No. 5,120,120 to Cohen.

Although these types of IOLs are somewhat suitable in reducing glare that occurs at the interfaces between lens sections having different refractive powers, these types of IOLs are unsuitable for reducing the halo effect or glare caused by light entering or exiting the perimeter of the IOL. These types of IOLs also fail to reduce reflection of light by the haptics used for mounting in the eye.

In addition, existing IOL's can block the flow of aqueous fluid, which generally flows from the back of the iris through iridectomies or holes in the iris through the pupil and into the anterior chamber. This blockage can cause glaucoma due to an increase in intraocular pressure.

Accordingly, a need exist for an IOL which reduces glare and the halo effect due to light entering or exiting its perimeter as well as light reflected off of its haptics, and which reduces intraocular pressure caused by a build up of fluid behind the iris.

SUMMARY OF THE INVENTION

An object of the present invention is to provide an IOL that is free of glare and the halo effect associated with conventional IOLs.

Another object of the present invention is to provide IOL that is suitable for implantation in an eye in place of or in addition to the natural lens of the eye, and which includes a light-absorbing material for absorbing undesirable light rays to eliminate glare and the halo effect experienced by the eye.

A further object of the invention is to provide a IOL system comprising a plurality of IOLs for implantation in an eye in place of or in addition to the natural lens of the eye, with each lens having a light-absorbing material to eliminate glare and the halo effect.

Still another object of the invention is to provide an IOL having a lens portion, a mounting apparatus, such as haptics, for mounting the lens portion in an eye, and a light-absorbing material at least at the perimeter of the lens portion and included in the haptics to eliminate glare and the halo effect caused by light reflecting from the haptics and light propagating towards the IOL at undesirable angles.

Yet another object of the invention is to provide an IOL having a openings or holes cut out of the IOL to allow aqueous fluid to pass from behind the iris through the IOL and into the anterior chamber, thus relieving intraocular pressure.

These and other objects of the present invention are substantially achieved by providing an intraocular lens, adapted for implantation into an eye to adjust a refractive power of an eye, comprising a lens portion and a light-absorbing material. The lens portion has first and second surfaces and a perimeter connecting the first and second surfaces which extends entirely about the lens portion. The light-absorbing material is disposed to absorb light propagating in a direction towards the perimeter, to thus eliminate glare and the halo effect caused by such light. The light absorbing material can be disposed to absorb substantially all of the light impinging on the perimeter, and can be disposed proximate to or at the perimeter and along substantially all or all of perimeter.

The intraocular lens can further include one of more haptics comprising a light-absorbing material which substantially eliminates reflection of light from the haptics, and thus reduces glare experienced by the eye. The intraocular lens can also include a third surface which extends transversely to the first and second surfaces to define an opening in or completely through the lens portion, and a second light-absorbing material which absorbs light propagating towards the third surface.

Additionally, the intraocular lens can be configured as an intraocular lens system comprising two or more intraocular lenses having the light absorbing material and features as described above for a single intraocular lens. The multiple intraocular lenses can be placed proximate or against one another when implanted in the eye, or can be configured to interlock when implanted. Also, each of the IOLs can have different refractive powers, or can include multiple refractive powers, to correct the specific vision disorder of the eye in which they are being implanted.

The intraocular lens can also be configured to have an opening or multiple openings through the lens or through a lens system comprised of two or more intraocular lenses. The lens system can have openings in each lens that align when the lens system is assembled either in the eye or before implantation in the eye and form a continuous passageway through the lens system.

BRIEF DESCRIPTION OF THE DRAWINGS

These and other objects, advantages and novel features of the present invention will be more readily appreciated from the following detailed description taken in conjunction with the accompanying drawings, of which:

FIG. 60 is an exploded perspective side view of the IOL system shown in FIG. 59;

FIG. 61 is a front view of the rear lens of the IOL system shown in FIG. 59;

DETAILED DESCRIPTION OF THE PREFERRED EMBODIMENTS

Figure 1:
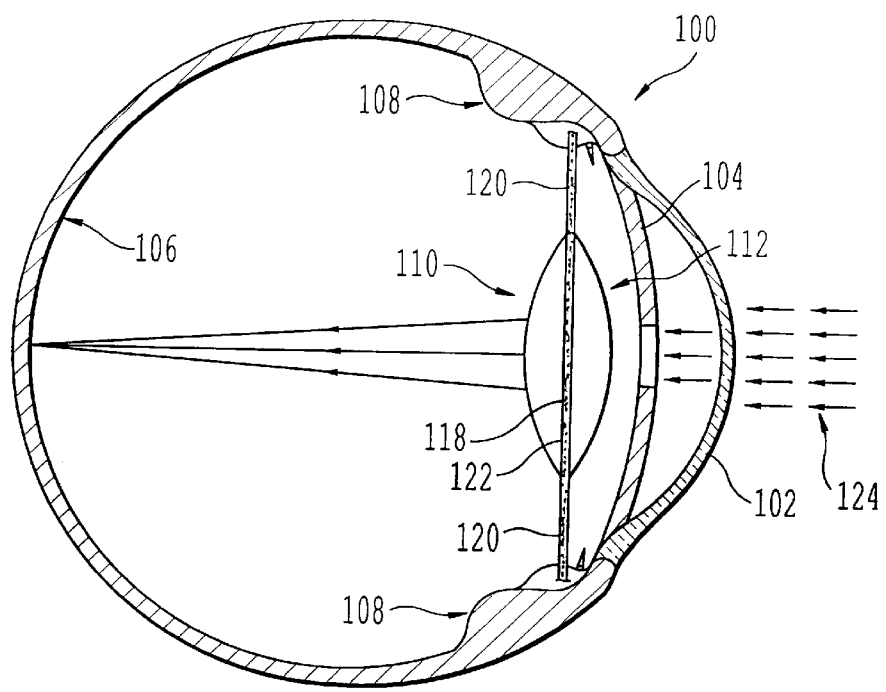
FIG. 1 is a cross-sectional view of an eye having an IOL according to an embodiment of the present innovation implanted therein.

An IOL according to an embodiment of the present invention as shown in FIGS. 1–4. Specifically, FIG. 1 shows a normal eye 100, which includes a cornea 102, an iris 104, a retina 106 and a ciliary sulcus 108. As further illustrated, an IOL 110 has been implanted in the eye 100 in place of the natural lens to correct for a vision disorder in the eye 100, such as myopia, hyperopia, astigmatism or the like.

Figure 3:
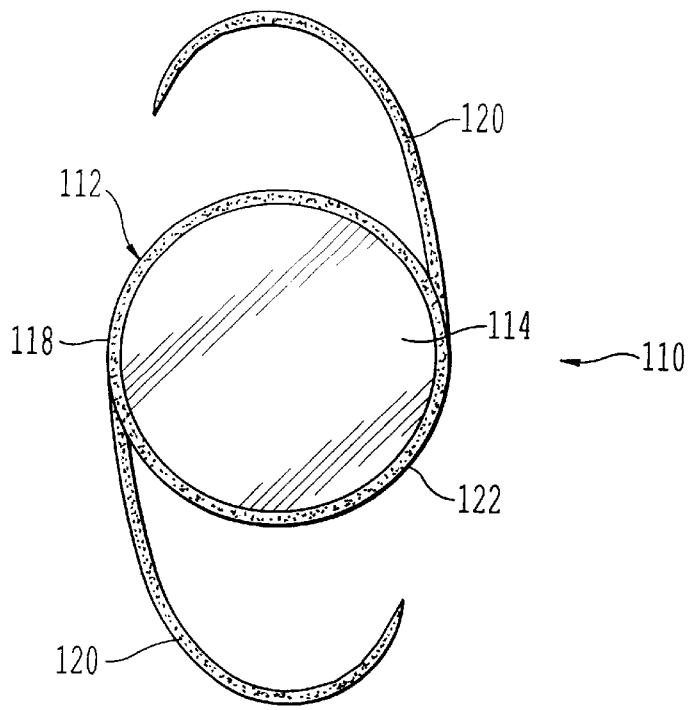
FIG. 3 is a front view of the IOL implanted in the eye as shown in FIGS. 1 and 2.
Figure 4:
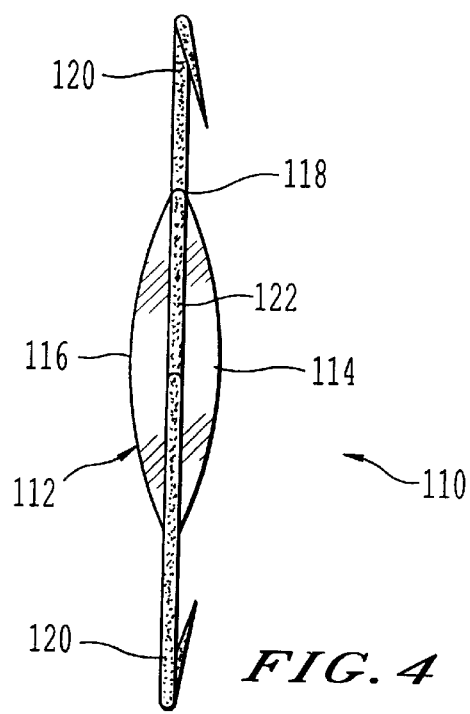
FIG. 4 is a side view of the IOL shown in FIG. 3.

As shown in more detail in FIGS. 3 and 4, the IOL 110 comprises a lens portion 112 including a first surface 114, a second surface 116 and a perimeter 118 connecting the first and second surfaces. The lens portion 112 can be made of a synthetic material such as silicone, polymethylmethacrylate, hydrogel, polysulfone, glass, or any other suitable material, and can have an outer diameter of, for example, about 1 mm to about 12 mm, or any other suitable diameter. Furthermore, the first surface 114, second surface 116, or both, can be concave, convex, planar, or have any other suitable shape or types of shapes for replacing the natural lens of the eye and, if necessary, for correcting the vision disorder of the eye 100 as appropriate.

The IOL further comprises haptics 120, which can be made of surgical steel or any other suitable non-biodegradable material. In this example, the haptics 120 attach to the ciliary sulcus 108 to mount the IOL 110 in the eye 100. As further illustrated, the IOL 110 includes a light absorbing material 122 which can be, for example, a dark pigment material mixed with plastic or silicone, or any other suitable material. In this example, the light-absorbing material 120 is a coating that is applied to the perimeter 118 of the lens portion 114 and can have a thickness of, for example, about 1 $\mu$m to 2,000 $\mu$m. The haptics 120 can also be coated with the light-absorbing material, or can be made to include the light-absorbing material or can be impregnated with the light absorbing material.

The light-absorbing material 120 can surround all or substantially all of the perimeter 118 of the lens portion 112, and can have any suitable width in relation to the width of the perimeter and the thickness of the lens portion 112. Furthermore, the light-absorbing material 120 need not be coated on the outside of the perimeter 118, but rather, can be impregnated into the perimeter 118, or impregnated into lens portion 112 along the perimeter 118 at a desired distance from the perimeter 118.

As light rays 124 enter the cornea 102 of the eye 100 as shown, for example, in FIG. 1, the cornea 102 and IOL 110 focus the light rays on to the retina 106 to create an image that is perceived by the eye. However, the light-absorbing material 120 of the lens portion 112 absorbs any light propagating toward the perimeter 118 in a direction into the lens portion 112, as well as any light being diffracted in the lens portion 112 toward perimeter 118. The light-absorbing material of the haptics 120 also prevents any or substantially any light impinging on the haptics 120 from being reflected by the haptics 120.

Accordingly, any glare that would be created by light reflected by the haptics 120, or by light leaving or entering the perimeter 118 of the lens portion 112, is absorbed and therefore not sensed by the retina 106. Therefore, the eye 100 does not perceive any type of glare and thus, does not suffer from the glare or halo effect associated with conventional IOLs discussed in the Background section above.

Figure 5:
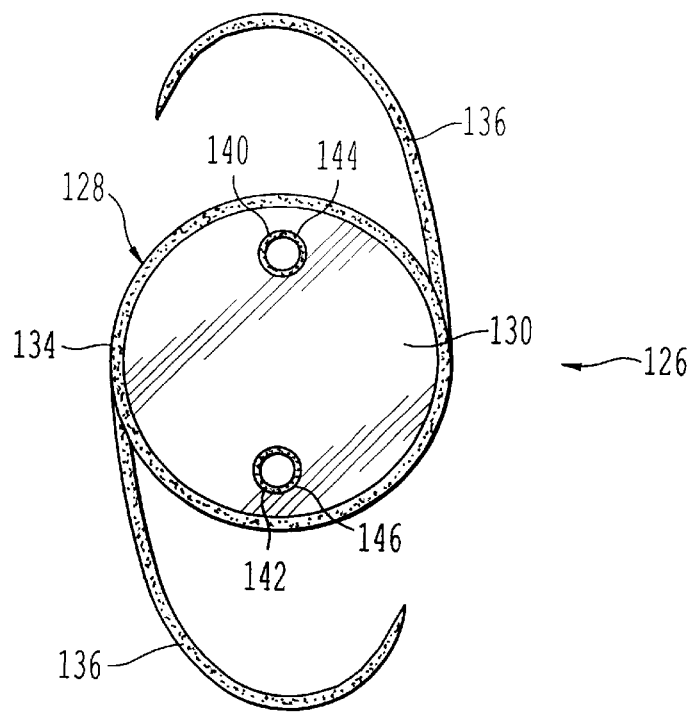
FIG. 5 is a front view of an IOL according to another embodiment of the present invention.
Figure 6:
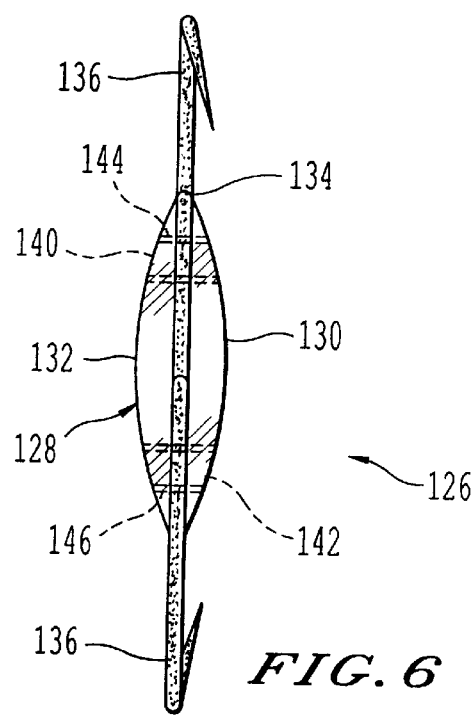
FIG. 6 is a side view of the IOL shown in FIG. 5.

Another embodiment of an IOL according to the present invention is shown in FIGS. 5 and 6. In this embodiment, IOL 126 is similar in all respects to IOL 110 discussed above. That is, IOL 126 includes a lens portion 128 having a first surface 130, a second surface 132 and a perimeter 134. The IOL 126 also includes haptics 136 and a light-absorbing material 138 that is disposed at, in or about the perimeter 134 in a manner similar to light absorbing material 122 discussed above with regard to IOL 110.

IOL 126 further includes a plurality of positioning holes 140 and 142 into which an instrument can be inserted to hold and adjust the position of the IOL 126 as it is being mounted in the eye. In this example, positioning holes 140 and 142 each pass entirely through lens portion 128 from first surface 130 to second surface 132. However, the positioning holes need not pass entirely through the lens portion 128, but rather, could merely be indentations in the first surface 130, the second surface 132, or both. Also, although only two positioning holes are shown, the lens portion 128 can include any suitable number of positioning holes.

As further illustrated, the positioning holes are defined by surfaces 144 and 146. In this example, the surfaces 144 and 146 are coated with the light-absorbing material 138 as shown, having any thickness within the range of thickness described above. However, the light-absorbing material 138 need not be present as coating surfaces 144 and 146, but rather could be impregnated into the surfaces 144 and 146, or can be impregnated in the lens portion 128 along surfaces 144 and 146.

As discussed above with regard to IOL 110, the light-absorbing material 138 at, in or along perimeter 134 absorbs light rays propagating in a direction toward perimeter 134 from outside the lens portion 128, as well as scattered light rays propagating toward the perimeter 134 from inside the lens 128. Also, the light-absorbing material at, in or along surfaces 144 and 146 absorbs light applied in a similar manner. Furthermore, the light-absorbing material of the haptics 136 also prevents light impinging on the haptics 136 from being reflected.

Figure 2:
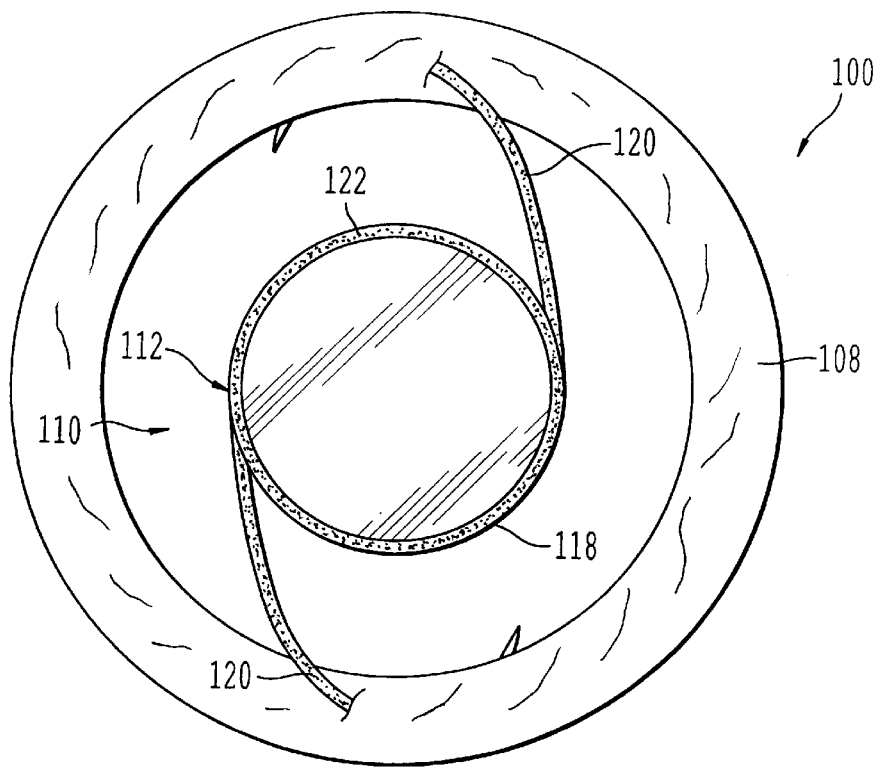
FIG. 2 is a front cross-sectional view of the eye and implanted IOL shown in FIG. 1.

The IOL 126 shown in FIGS. 5 and 6 can be implanted in an eye 100 in a manner similar to that in which IOL 110 is implanted as shown, for example, in FIGS. 1 and 2, IOL 126 will therefore eliminate glare and the halo effect due to the presence of light-absorbing material 138 at the perimeter 134, at the haptics 136, and at the positioning holes 140 and 142.

Figure 7:
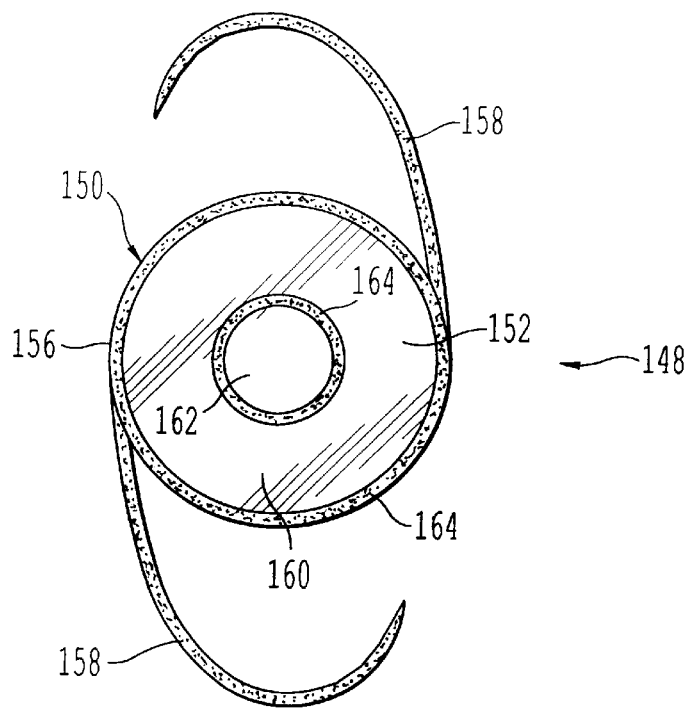
FIG. 7 is a front view of an IOL according to a further embodiment of the present invention.
Figure 8:
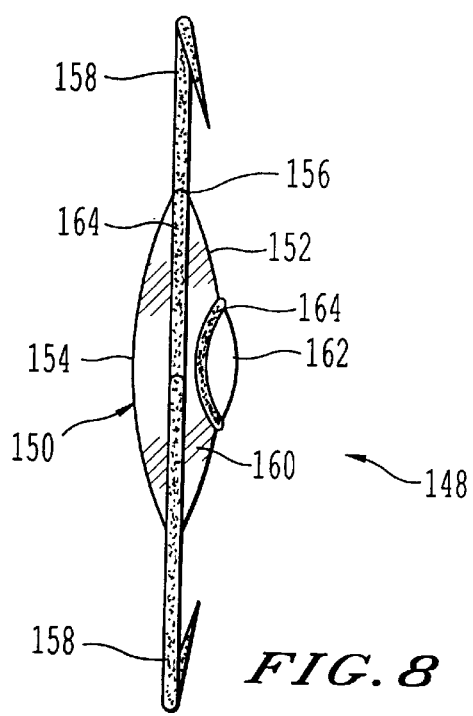
FIG. 8 is a side view of the IOL shown in FIG. 7.

An IOL according to another embodiment of the present invention can include regions having different refractive powers so as to act as, for example, as a multi-focal lens, such as a bi-focal lens. As shown in FIGS. 7 and 8, an intraocular lens 148 according to this embodiment includes a lens portion 150 having a first surface 152, a second surface 154 and a perimeter 156 connecting the first and second surfaces. The lens portion 150 is generally similar in all respects to the lens portions described above, and can be mounted into eye 100 in a manner similar to the IOLs described above. The IOL 148 also includes haptics 158 similar to those described above for IOL 110.

However, unlike the IOLs described above, first surface 152, second surface 154, or both, include first and second refractive portions having first and second respective refractive powers. For exemplary purposes, the first surface 152 is shown as having a first refractive portion 160 and a second refractive portion 162. Similar to IOL 110 discussed above, a light-absorbing material 164 is disposed on or at the perimeter 156 of IOL 148. This light-absorbing 164 can be similar to light-absorbing material 122 described above, and can be applied as a layer onto perimeter 156, impregnated into perimeter 156, or impregnating into lens portion 150 along perimeter 156 at a distance from perimeter 156.

In addition, the light-absorbing material 164 is disposed at the interface between first refractive portion 160 and second refractive portion 162 as illustrated. In this example, the light-absorbing material 164 can be applied to the first surface at the interface between first refractive portion 160 and second refractive portion 162, or can be impregnated into lens portion 156 at that interface. Accordingly, the light-absorbing material 164 at the perimeter 156 absorbs light propagating toward the perimeter 156, as well as light scattered in the lens portion 150 towards the perimeter 156. The light-absorbing material on the haptics 160 absorbs light impinging on the haptics so that the haptics 160 do not reflect that light. Accordingly, the light-absorbing material 164 prevents the eye into which IOL 148 is mounted from experiencing glare and the halo effect due to the presence of the IOL 148.

Figure 9:
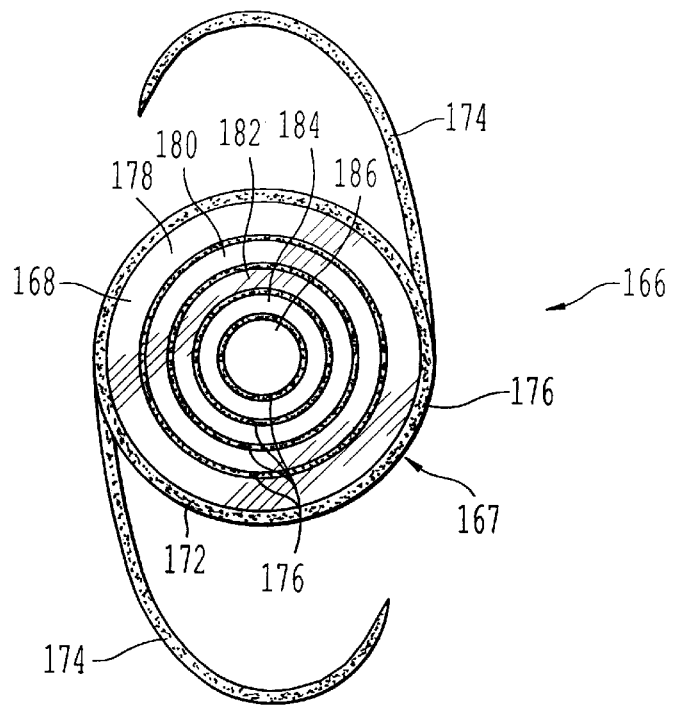
FIG. 9 is a front view of an IOL according to another embodiment of the present invention.
Figure 10:
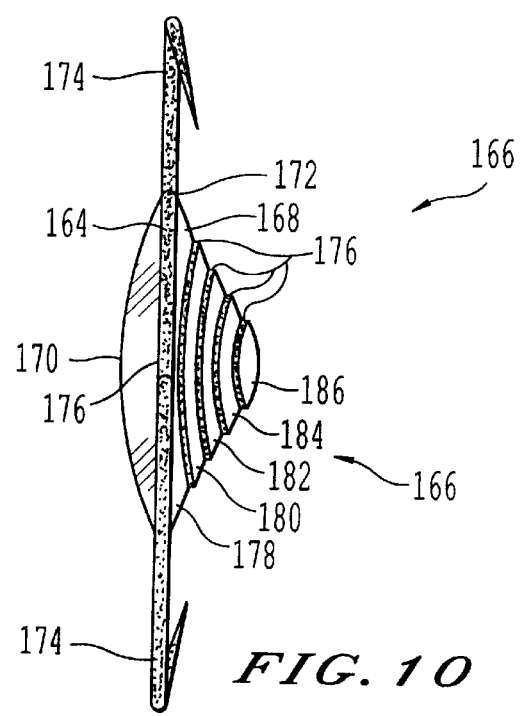
FIG. 10 is a side view of the IOL shown in FIG. 9.

As stated above, an intraocular lens can include more than two portions having different refractive powers. For example, as shown in the embodiment illustrated in FIGS. 9 and 10, IOL 166 is generally similar in size, shape and construction to the IOLs discussed above, and can be implanted into eye 100 in a manner similar to IOL 110 discussed above. That is, IOL 166 includes a lens portion 167 having a first surface 168, a second surface 170, and a perimeter 172 connecting first surface 168 to second surface 170. IOL 166 also includes haptics 174, and a light-absorbing material 176 disposed on, in or proximate to perimeter 172 in a manner similar to that described above with regard to IOL 110.

However, unlike the IOLs discussed above, IOL 166 includes multiple regions having different refractive powers. In this example, first surface 168 includes first, second, third, forth, and fifth refractive regions 178, 180, 182, 184, and 186, respectively, each having different respective shapes and thus different refractive powers. As in IOL 148 shown in FIGS. 7 and 8, light-absorbing material 176 is present at each of the interfaces between adjacent refractive regions 178–186. The light-absorbing material 176 can be applied as a layer to first surface 168 at the refractive regions, or can impregnated into the lens portion 167.

Figure 11:
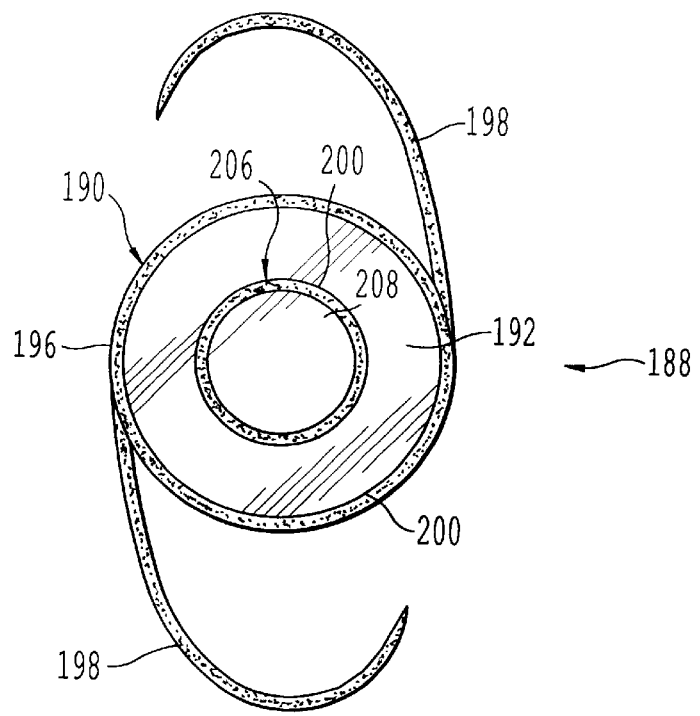
FIG. 11 is front view an IOL system including two IOLs according to an embodiment of the present invention.
Figure 12:
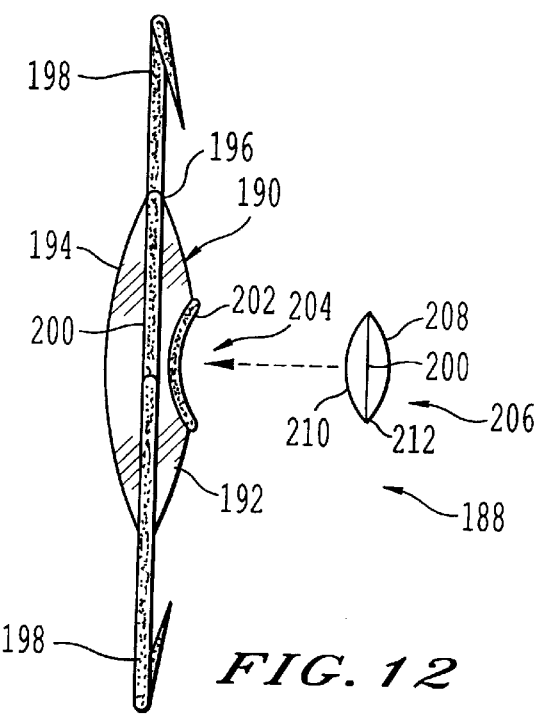
FIG. 12 is an exploded side view of the IOL lens system shown in FIG. 11.

Each of the IOLs discussed above include a single lens portion. However, the IOLs can be configured as lens systems having multiple lens portions. For example, as shown in FIGS. 11 and 12, IOL system 188 includes a first lens portion 190 similar in size, shape and construction to the lens portion of any IOL discussed above. That is, first lens portion 190 has a first surface 192, a second surface 194 and perimeter 196 similar to the IOLs discussed above. In this example, the first surface 192 and second surface 194 can be shaped for far or near refractive power. IOL system 188 also includes haptics 198 which are similar to haptics 120 described above, and are connected to first lens portion 190.

Additionally, as with the IOLs described above, a light-absorbing material 200 is disposed on, in, or proximate to perimeter 196 of the first lens portion 190. However, unlike the IOLs discussed above, first lens portion 190 also includes a third surface 202 forming an opening 204 in the first lens portion 190. The third surface 202 can pass entirely through first lens portion 190 so that opening 204 passes entirely through first lens portion 190. Alternatively, third surface 202 can form a recess in first surface 192, second surface 194, or both, so that opening 204 is shaped as recess as in either or both first and second surfaces 192 and 194. The diameter of opening 204 can be, for example, 0.50 mm through 3.00 mm, or any other suitable diameter. Also, light-absorbing material 200 is applied on, in, or proximate surface 202 to absorb light in a manner similar to the light-absorbing materials described above.

As further shown in FIGS. 11 and 12, IOL 188 includes a second lens portion 206 having a first surface 208, a second surface 210 and a perimeter 212 connecting first and second surfaces 208 and 210 respectively. The second lens portion 206 has an outer diameter which enables it to fit within opening 204 in the first lens potion 190. That is, the second lens portion 206 can fit entirely into the opening 204, or alternatively, can be shaped so that only a portion of it fits in opening 204. The second lens portion 206 can interlockingly couple with the third surface 202. Alternatively, the perimeter 212 can have threads which engage with threads in the third surface 202 so that the second lens portion 206 screws into opening 204. The second lens portion 206 can also be held in the opening 204 by an adhesive, or in any other suitable manner. Further, light-absorbing material 200 can be applied on, in or proximate to the perimeter 212 of the second lens portion 206 in a manner similar to the light absorbing materials described above. Accordingly, the light-absorbing material 200 of first lens portion 190 and second lens portion 206 functions as the light-absorbing materials described above to absorb unwanted light, and thus eliminate glare and the halo effect in an eye into which IOL system 188 is implanted.

Figure 13:
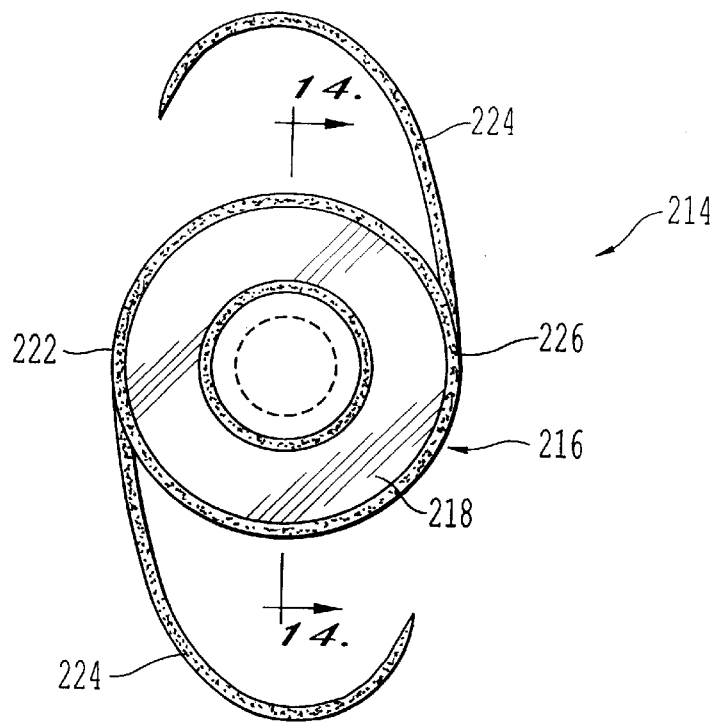
FIG. 13 is a front view of an IOL lens system according to another embodiment of the present invention.
Figure 14:
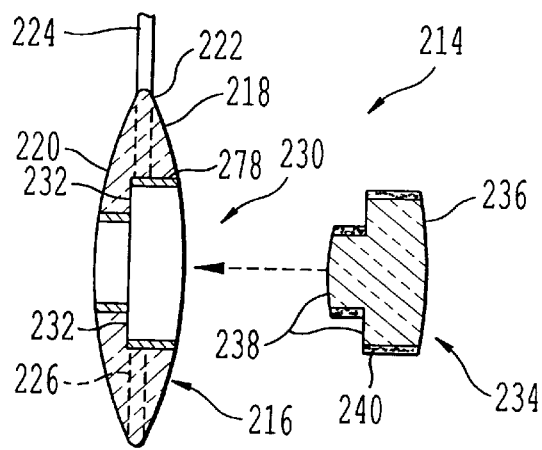
FIG. 14 is an exploded side view of the IOL lens system shown in FIG. 13.

Although the second lens portion 206 is shown in FIGS. 11 and 12 as being circular or substantially circular, the second lens portion 206 can have any suitable shape. For example, as shown in FIGS. 13 and 14, IOL system 214 includes a first lens portion 216 having a first surface 218, a second surface 220 and a perimeter 222 similar to the first and second surface and perimeter of first lens portion 190. IOL 214 also includes haptics 224 coupled to first lens portion 216. A light-absorbing material 226 is applied on, in or proximate to the perimeter 222 of first lens portion 216.

First lens portion 216 also includes a third surface 228 forming a opening 230 which, in this example, passes entirely through the first lens portion 216. However, the first surface 228 is shaped to form a stepped surface 232 as shown. The second lens portion 234 of IOL system 214 has a first surface 236 and a second stepped surface 238, as well as a perimeter 240 which connects the first surface 236 and the second surface 238. Accordingly, the second stepped surface 238 can engage with the stepped surface 232 of first lens portion 216 when the second lens portion 234 is inserted into opening 230. The second lens portion 234 could alternatively be screwed into the opening 230 or held in the opening 230 by an adhesive in a manner similar to second lens portion 206 described above.

Also, like second lens portion 206 described above, second lens portion 234 includes light-absorbing material 226 which is applied on, in or proximate to its perimeter 240 and perimeter of stepped surface 238 as shown. Accordingly, the light-absorbing material 226 functions in a manner similar to the light-absorbing materials described above to absorb unwanted light and thus eliminate glare and the halo effect experienced by an eye into which the IOL system 214 is implanted.

Figure 15:
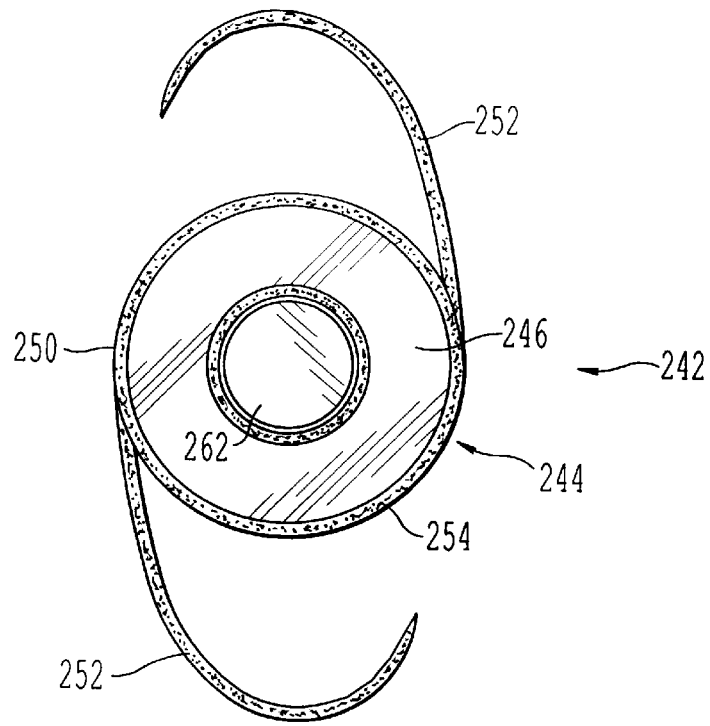
FIG. 15 is a front view of a IOL system according to a further embodiment of the present invention.
Figure 16:
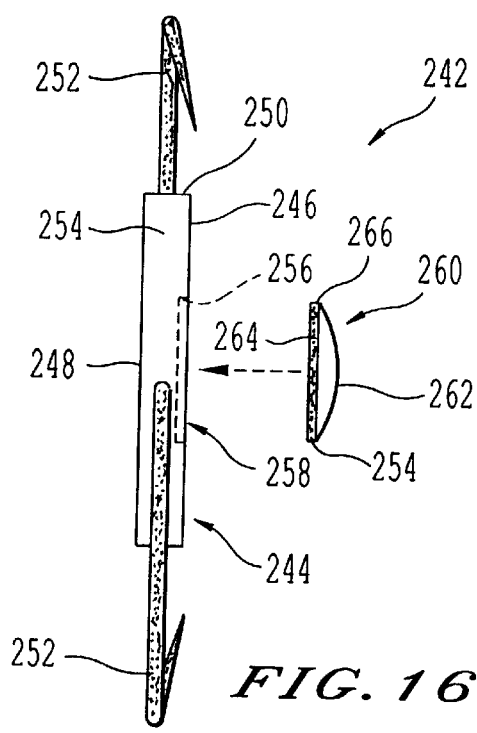
FIG. 16 is an exploded side view of the IOL system shown in FIG. 15.

In addition, although the first lens portion 190 of the IOL 188 shown in FIGS. 11 and 12 has a refractive power, the lens portion can be formed to have no refractive power as shown, for example, in FIGS. 15 and 16. Specifically, IOL system 242 includes a first lens portion 244 similar in overall size and construction to first lens portion 190 described above. First lens portion 244 includes a first surface 246, a second surface 248 and perimeter 250 connecting first surface 246 and second surface 248. However, unlike the first and second surfaces of first lens portion 190 described above, first surface 146 and second surface 148 are each planar or substantially planar and do not have any or substantially any refractive power.

As in the IOLs described above, haptics 252 are attached to first lens portion 244 for mounting the IOL into an eye in a manner similar to that for the IOLs described above. Furthermore, a light-absorbing material 254 similar to those described above is disposed on, in or proximate to the perimeter 250 of first lens portion 244.

First lens portion 244 also includes a third surface 256 forming an opening 258 that passes into or entirely through first portion 244. In other words, as with first lens portion 190 described above, third surface 256 can connect first surface 246 to second surface 248. Additionally, light-absorbing material 254 is applied to first surface 256 for reasons similar to those described above.

The IOL system 242 further includes a second lens portion 260 which is generally similar in overall size and shape to second lens portion 206 described above. The second lens portion 260 can be shaped to have a refractive power of, for example, about plus 1 to about plus 3 diopters, or about minus 1 to about minus 3 diopters, or any other suitable power. Thus, the second lens portion 260 can be used to correct near or far vision and thus make the lens system 242 into a bifocal type lens system.

As shown, second lens portion 260 has a first surface 262, a second surface 264 and a perimeter 266 connecting the first surface 262 to the second surface 264. As described above, the first and second surfaces can be shaped appropriately to provide the second lens portion 260 with the appropriate amount of plus or minus dioptic power. The second lens portion 260 can be mounted into opening 258 in a manner similar to second lens portions 206 and 234 described above. Furthermore, light-absorbing material 254 can be applied on, in or proximate to perimeter 266 to absorb unwanted light as described above. Accordingly, the light-absorbing material 252 applied to the perimeters of first lens portion 244 and second lens portion 260, as well as the light-absorbing of haptic 252, absorb unwanted light to eliminate glare and the halo effect experienced by an eye into which intraocular lens system 242 is implanted.

Figure 17:
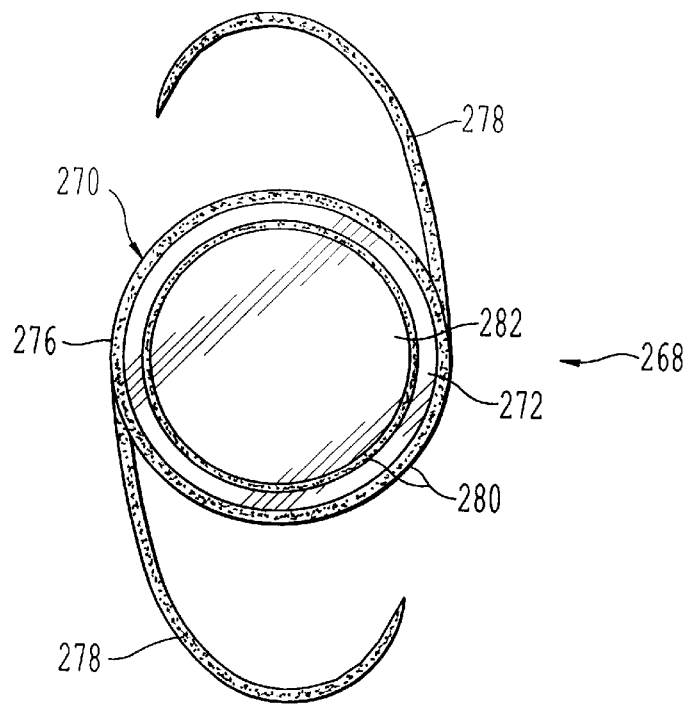
FIG. 17 is a front view of a piggyback IOL system including two lenses according to another embodiment of the present invention.
Figure 18:
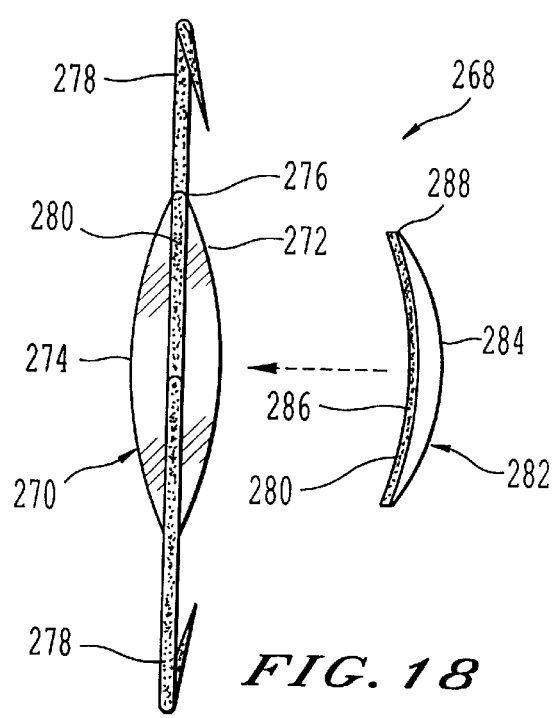
FIG. 18 is an exploded side view of the piggyback IOL lens system shown in FIG. 17.

The IOL system also can be configured as a piggyback lens system as will now be described. Specifically, as shown in FIGS. 17 and 18, an IOL system 268 can include a first lens portion 270 having a first surface 272, a second surface 274 and perimeter 276 similar to, for example, lens portion 274 described above. Also, lens system 268 can include haptics 278 that are attached to first lens portion 270 to mount the lens system 268 in an eye in a manner similar to that for IOL 110. Additionally, a light absorbing material 280 similar to those described above is disposed on, in or proximate to the perimeter 276 of first lens portion 270 to absorb unwanted light in a manner similar to that described above.

Lens 268 further can include a piggyback lens 282 which can be mounted to first lens portion 270. Specifically, piggyback lens 282 can have a refractive power which is, for example, different than that of first lens portion 278, and includes a first surface 284, a second surface 286 and perimeter 288. The first and second surfaces 284 and 286 can be concave, convex, planar, or any other suitable shape. Also, light-absorbing material 280 can be applied on, in or proximate to perimeter 288 to absorb unwanted light in a manner describe above.

The second lens portion 282 can be piggybacked onto first lens portion 270 by attaching second surface 286 of piggyback lens portion 282 to first surface 272 of first lens portion 270 as shown. An adhesive can be used to attach the piggyback lens 282 to first lens portion 270. Further details of different types of piggyback lens systems are exemplified in U.S. patent application Ser. No. 09/178,739 referenced above, and it is noted that the types of light absorbing materials described above can be applied on, in or proximate to the perimeters and refractive interfaces of the lenses described in this referenced patent application to eliminate glare and the halo effect experienced by eyes into which those types of lenses are implanted.

Figure 19:
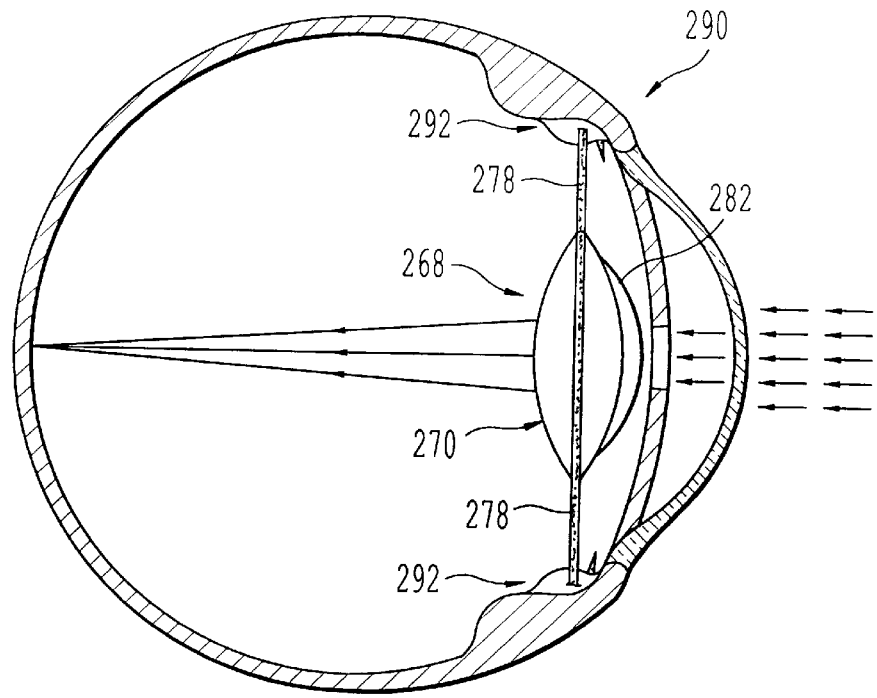
FIG. 19 is a cross-sectional view of an eye including the piggyback IOL system shown in FIGS. 17 and 18.
Figure 20:
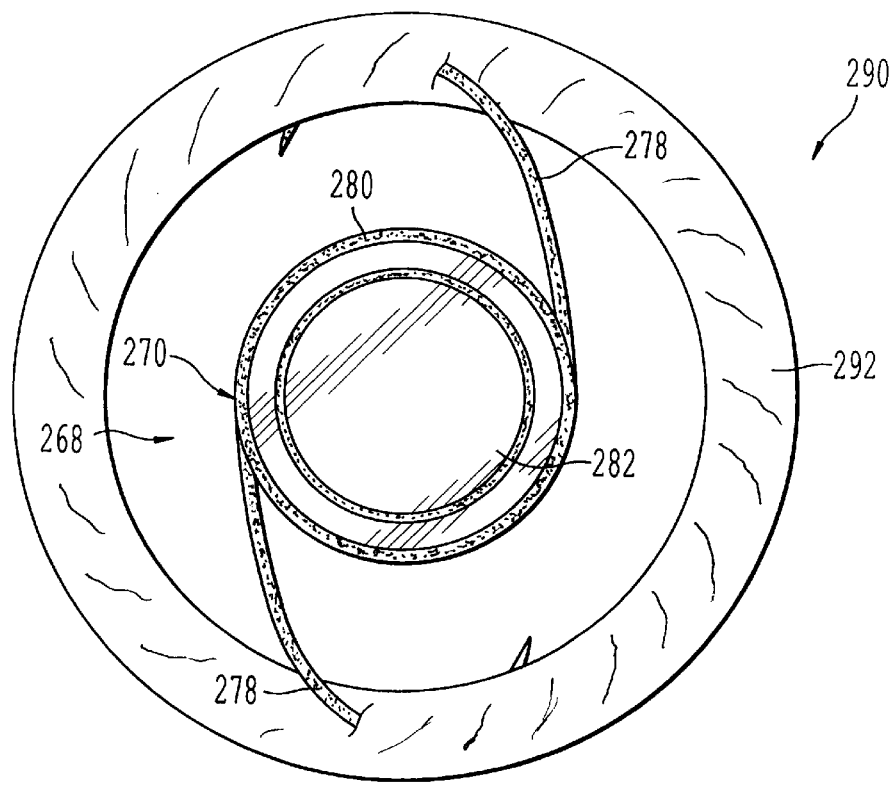
FIG. 20 is a front cross-sectional view of the eye and implanted piggyback lenses system shown in FIG. 19.

Once the first lens portion 270 and piggyback lens portion 288 are coupled together, the lens system 268 can be implanted into an eye 290 by attaching haptics 278 to the ciliary sulcus 292 of the eye 290 as shown in FIGS. 19 and 20. Accordingly, the light-absorbing material on the perimeters of first lens portion 270 and piggyback lens portion 280, as well as the light-absorbing material of haptics 278, absorb unwanted light and thus eliminate glare and the halo effect experienced by eye 290.

Figure 21:
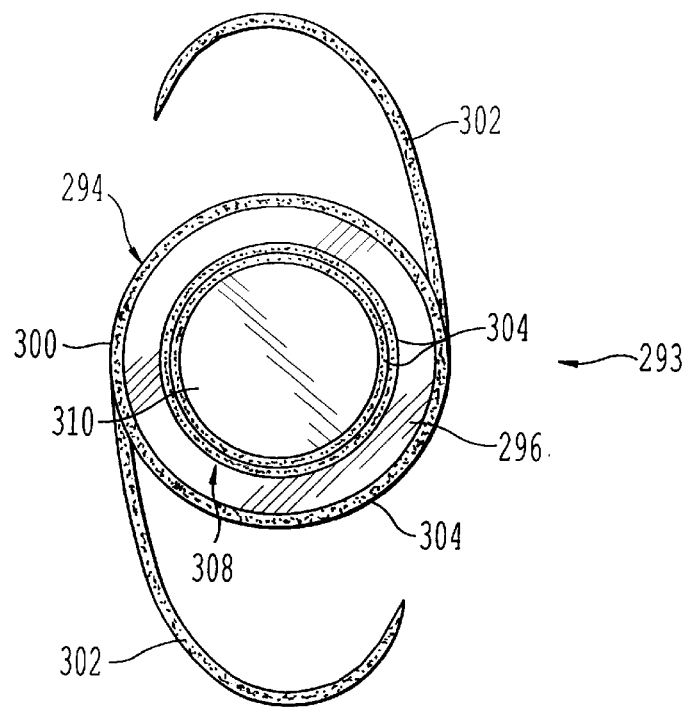
FIG. 21 is a front view of another piggyback IOL according to a further embodiment of the present invention.
Figure 22:
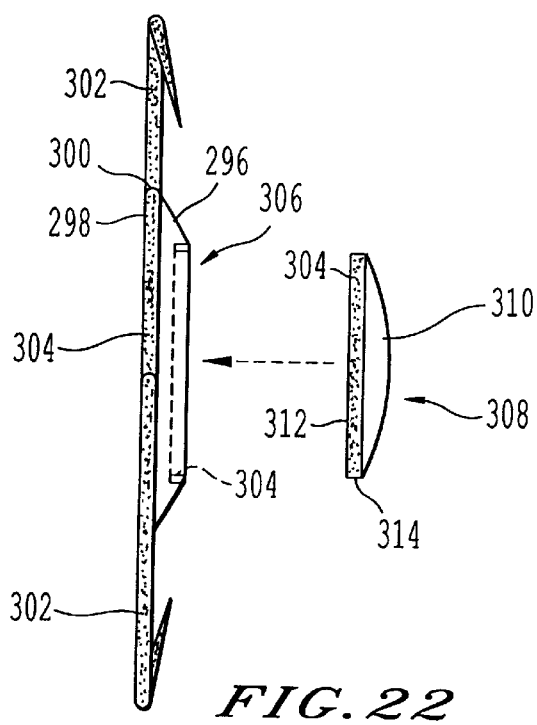
FIG. 22 is an exploded side view of the piggyback IOL system shown in FIG. 21.

As described above, piggyback 282 can be mounted to first lens portion 278 by, for example, an adhesive. Alternatively, as shown in FIGS. 21 and 22, piggyback lens system 293 can be configured so that the piggyback lens interlocks with the first lens portion. Specifically, the first lens portion 294 can include a first surface 296, a second surface 298 and a perimeter 300 connecting the first and second surfaces. Haptics 302 can be attached to the first lens portion 290 for mounting the lens system 293 into an eye in a manner similar to that described above. Also, the light-absorbing material 304 similar to those described above can be disposed on, in or proximate to the perimeter 300 to absorb unwanted light in the manner described above.

Furthermore, first lens portion 294 can include a recessed portion 306 in first surface 296. The light-absorbing material 304 can be applied to this recessed portion 306 about the perimeter of the surface forming the recess portion as shown. As further illustrated, second lens portion 308 includes a first surface 310, a second surface 312 and perimeter 314. The first and second surfaces 310 and 312 can have any suitable shape to provide the second lens portion 308 with any suitable refractive power. Light-absorbing material 304 can be applied on, in or proximate to perimeter 314 in a manner similar to that described above.

Second lens portion 308 can therefore function as a piggyback lens to interlock with first lens portion 294 and recess portion 306. Once piggyback lens portion 308 is attached to first lens portion 294, the IOL system can be implanted into an eye in a manner similar to IOL system 268 as shown, in example, in FIGS. 19 and 20.

Figure 23:
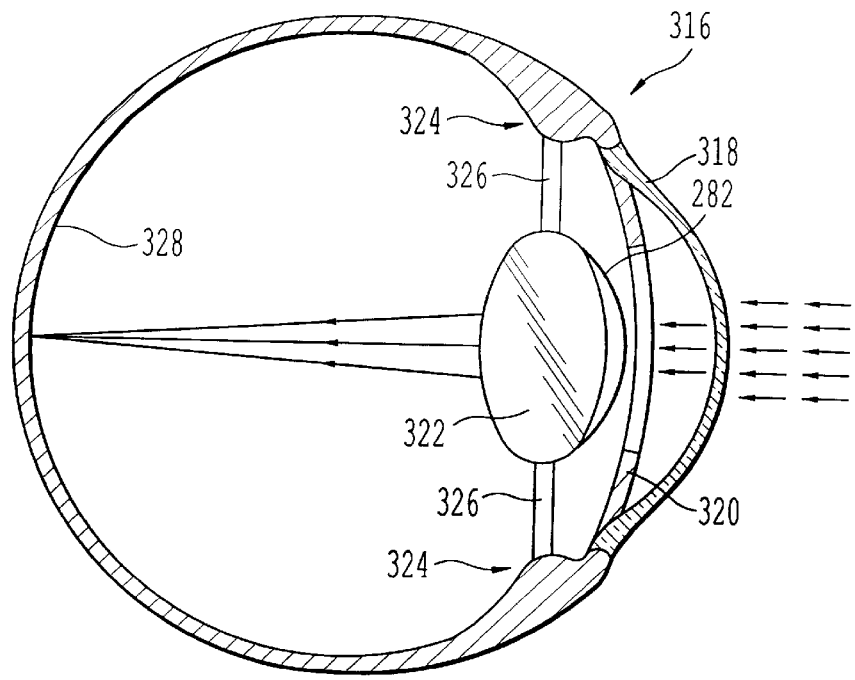
FIG. 23 is a cross-sectional view of an eye including a piggyback IOL according to another embodiment of the present invention.
Figure 24:
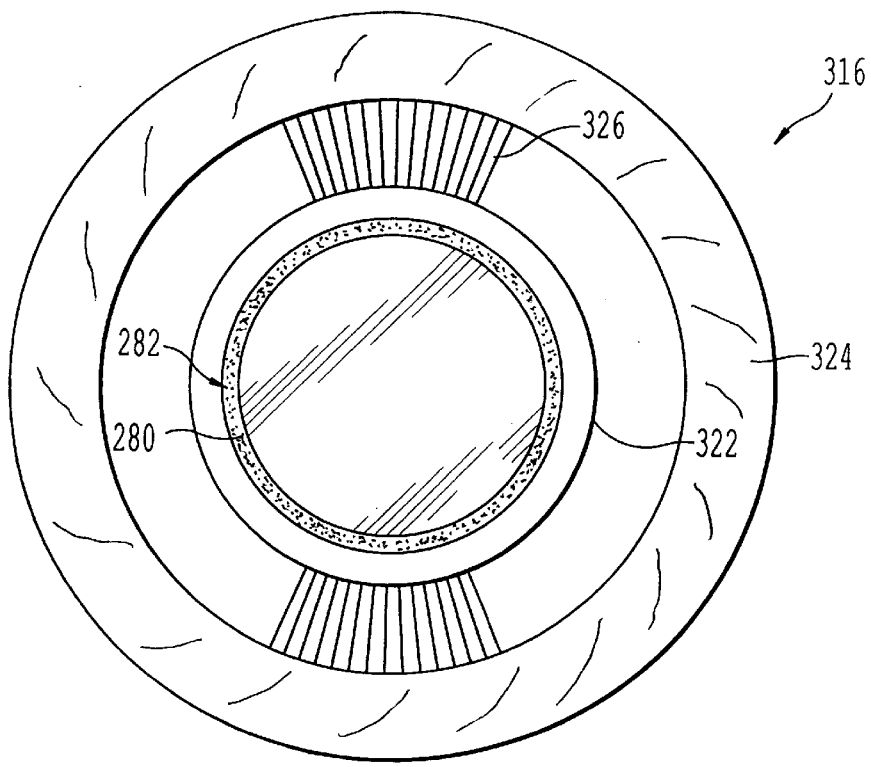
FIG. 24 is a front cross-sectional view of the eye and implanted piggyback IOL as shown in FIG. 23.

Furthermore, it is noted that any of the IOLs and IOL systems described above need not include haptics, but rather can be mounted directly to the natural lens of the eye, and therefore act as a piggyback lens for the natural lens of the eye. For example, FIGS. 23 and 24 show an eye 316 having a cornea 318, an iris 320, a lens 322 held in the eye 316 by the ciliary sulcus 324 and zonular ligament, and a retina 328. In this example, the second lens portion 308 of IOL system 282 (see FIGS. 17 and 18) is mounted directly to the front surface of the lens 322 by an adhesive or any other suitable method. Also, the first or second lens portions of any of the IOLs described above can be mounted to the front surface of lens 322 in this manner. Alternatively, the haptics attached to the lenses of those lens systems can be attached to, for example the ciliary sulcus 324 to mount the lens or lens systems onto the front surface of the lens 322. Different examples of piggyback configurations can be found in U.S. patent application Ser. No. 09/178,739 referenced above.

Figure 25:
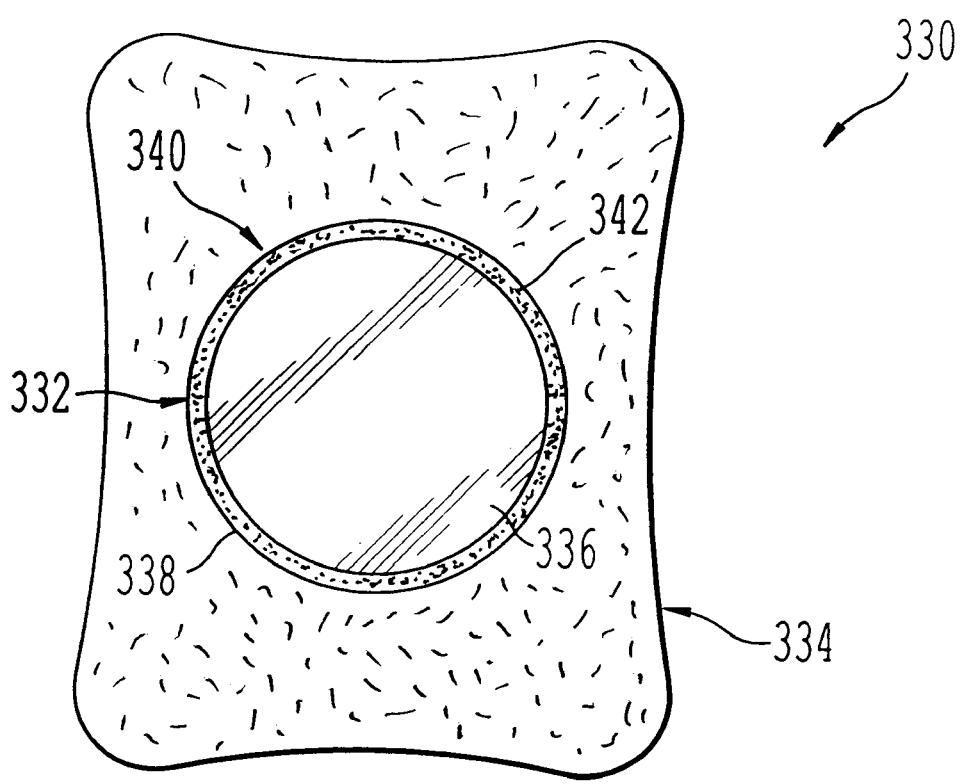
FIG. 25 is a front view of an IOL including a flexible mounting structure according to an embodiment of a present invention.
Figure 26:
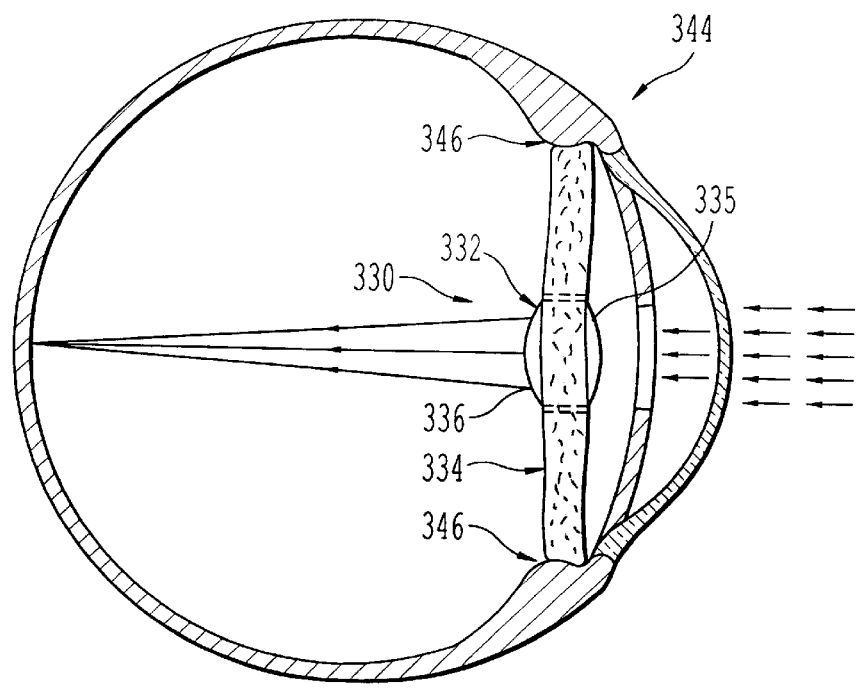
FIG. 26 is a cross-sectional view of an eye having the IOL shown in FIG. 25 mounted therein.
Figure 27:
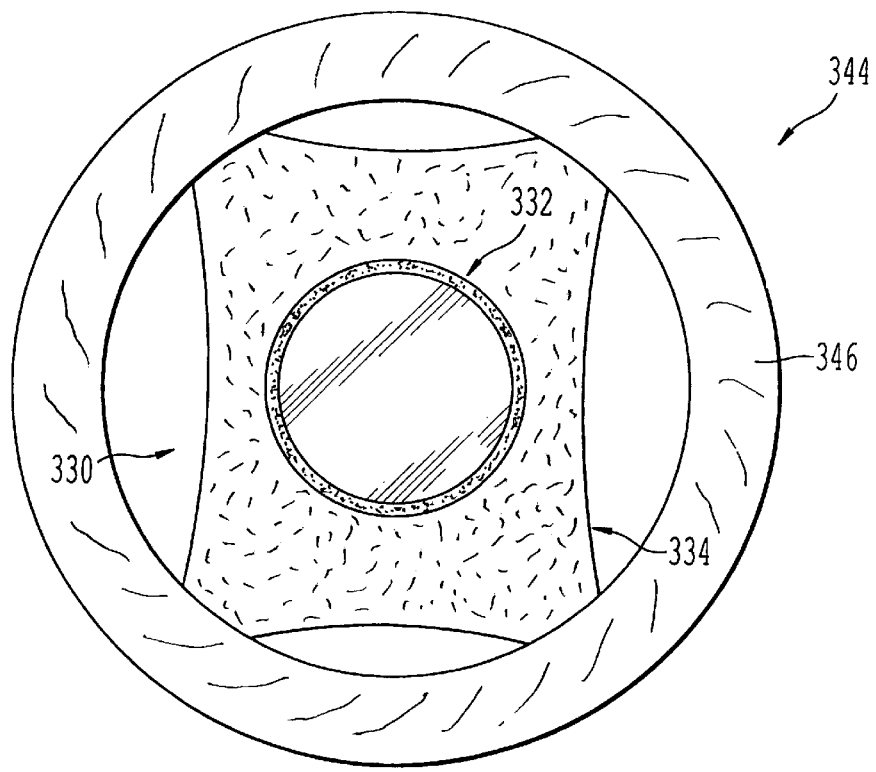
FIG. 27 is a front cross-sectional view of the eye and implanted IOL as shown in FIG. 26.
Figure 28:
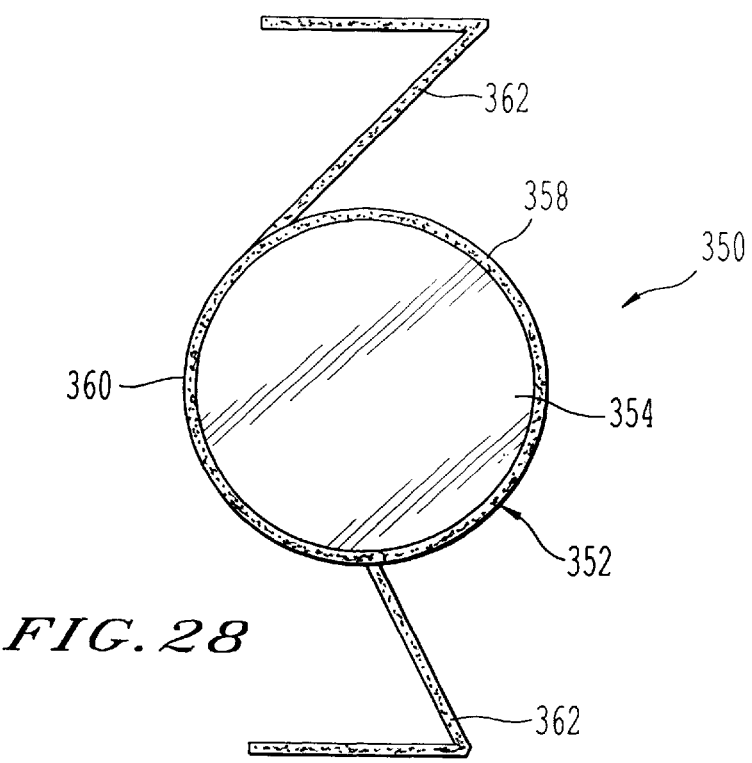
FIG. 28 is a front view of an IOL for mounting in the anterior chamber of an eye according to an embodiment of the present invention.
Figure 29:
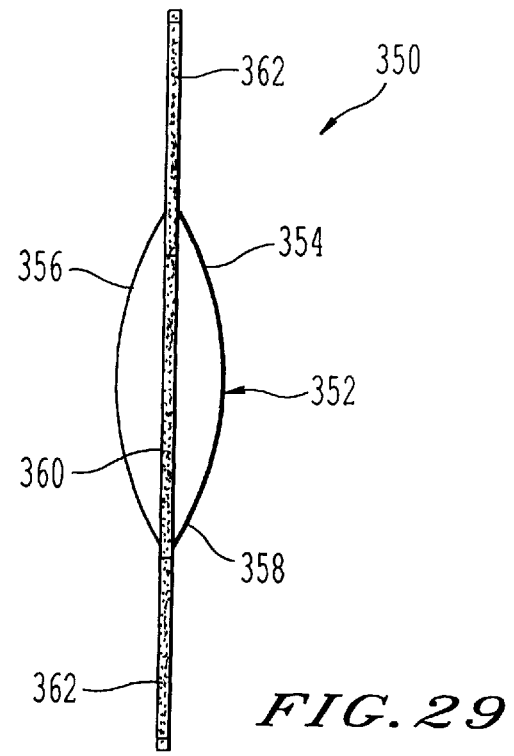
FIG. 29 is a side view of the IOL shown in FIG. 28.
Figure 30:
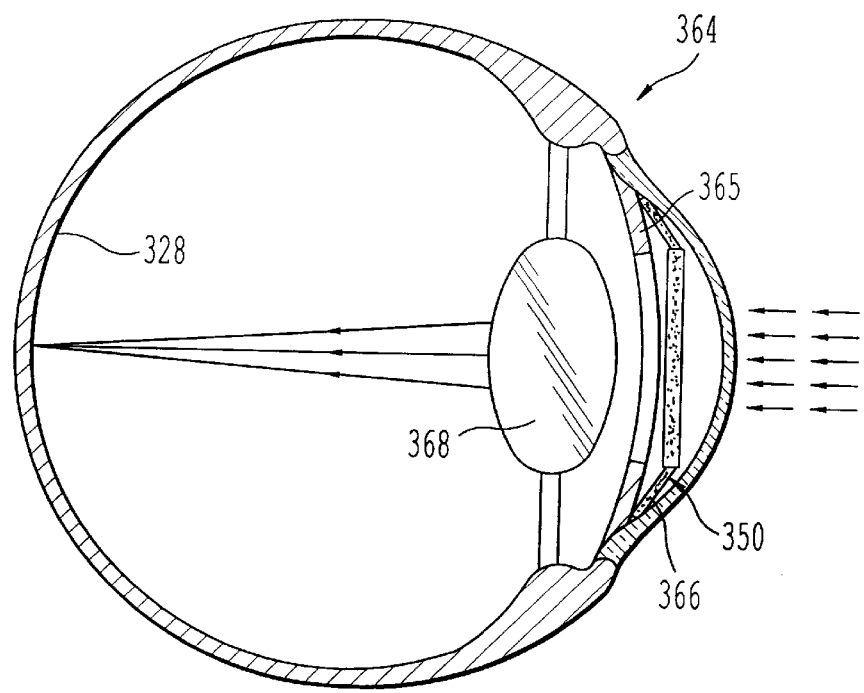
FIG. 30 is a cross-sectional view of an eye having an IOL as shown in FIGS. 28 and 29 mounted therein.
Figure 31:
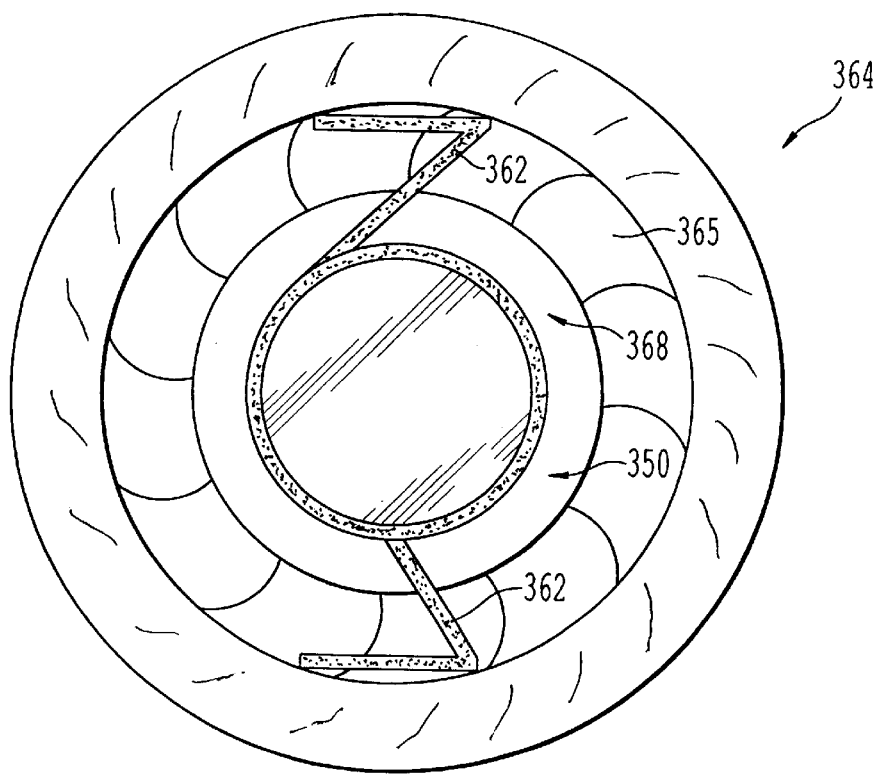
FIG. 31 is a front cross-sectional view of the eye and IOL as shown in FIG. 30.

Furthermore, any of the IOLs or IOL systems described above can include different types of mounting arrangements to mount into the posterior or anterior chamber of an eye. For example, as shown in FIGS. 25–27, the IOL can be configured as IOL 330 having a lens portion 332 and a lens mounting portion 334. As in the IOLs and IOL systems described above, lens portion 332 includes a first surface 334, a second surface 336 and a perimeter 338 connecting the first and second surfaces 334 and 336, respectively. The first and second surfaces 334 and 336 can have any suitable shape to provide the lens portion 334 with any suitable refractive power.

Lens mounting portion 334 includes an opening 340 into which the lens portion 332 is mounted by, for example, an adhesive, an interlocking arrangement, or in any other suitable manner. Lens mounting portion 334 can be made of a flexible material, such as silicon or any other suitable polymer, and can include a light absorbing material similar to those described above. Additionally, a light absorbing material 342 similar to those described above can be disposed on, in or proximate to the perimeter 338 of lens portion 332 to absorb unwanted light in a manner similar to the dark materials described above. As shown in FIGS. 26 and 27, the IOL 330 can be mounted into an eye 344 in place of the natural lens of the eye. In this example, the outer ends of lens mounting portion 334 fit against the ciliary sulcus 346 of the eye 344 to mount the IOL 340 in the posterior chamber of the eye 344.

Alternatively, the IOL can be configured as a lens, which is mounted in the anterior chamber of an eye. For example, as shown in FIGS. 28–31, IOL 350 includes a lens portion 352 which is generally similar in overall size and shape to those described above and has a first surface 354, a second 356 and perimeter connecting the first surface 354 to the second surface 356. The first and second surfaces 354 and 356 can have any suitable shape to provide the lens portion 352 with any suitable refractive power. A light absorbing material 360 similar to the light absorbing materials describe above can be disposed on, in or proximate to the perimeter 358 of the lens portion 352.

As further shown, the lens portion 352 is mounted to a haptic arrangement 362 that includes or is made of a light absorbing material. The haptic arrangement 362 is suitable for mounting the IOL 350 into the interior chamber of an eye as shown, for example, in FIGS. 30 and 31. Specifically, the ends of haptic arrangement 362 can contact the inner surface of the eye 364 in front of the iris 365 which forms the anterior chamber 366 of the eye. In this event, the IOL 350 can be inserted in addition to the natural lens 368 of the eye 364, or in place of the natural 368 if the natural lens 368 has been removed. Also, as described above, the light-absorbing material of the lens portion 352 and the haptic arrangement 362 absorbs unwanted light to therefore eliminate glare and the halo effect by the eye 364.

An IOL can also include a claw-type arrangement for mounting in the interior chamber of an eye. For example, as shown in FIGS. 32–35, IOL 370 includes a lens portion 372, which is generally similar in overall size and shape to the lens portions described above and includes a first surface 374, a second surface 376, and a perimeter 378 connecting the first surface 374 to the second surface 376. A light-absorbing material 380 similar to those described above can be disposed on, in or proximate to the perimeter 378 of the lens portion 372.

As further illustrated the IOL 370 include a lens mounting portion 382 having an opening 384 therein into which the lens portion 372 is mounted and secured by, for example, and adhesive, an interlocking arrangement or in any other suitable manner. The lens mounting portion 384 is made of a flexible material and includes a light-absorbing material similar to those described above.

As further illustrated, lens mounting portion 382 includes claw portions 386 and 388 which are adapted to attach to, for example, the iris of an eye to mount the IOL 370 in the interior chamber of an eye. The claw portions 386 and 388 define respective openings 390 and 392 as shown. The surfaces of the claw portions 386 and 388 defining these openings 390 and 392 are also coated with a light absorbing material 380 of the types described above.

Figure 32:
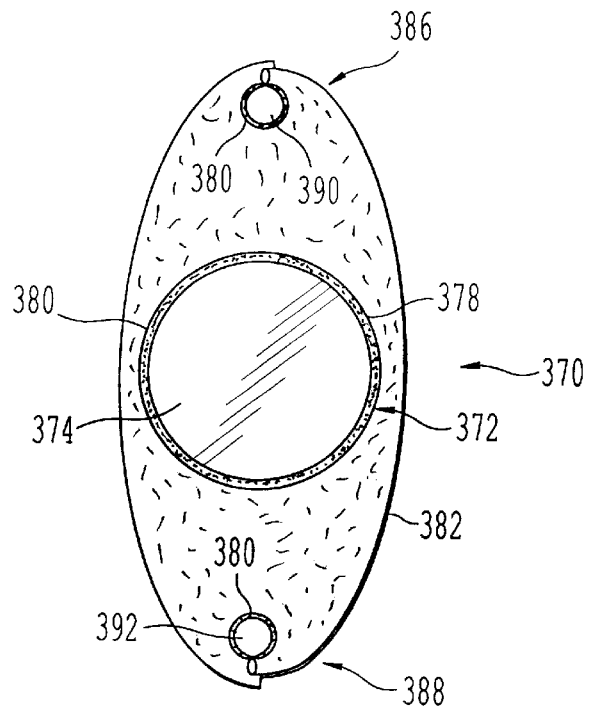
FIG. 32 is a front view of an IOL having a claw-type attachment structure according to an embodiment of the present invention.
Figure 33:
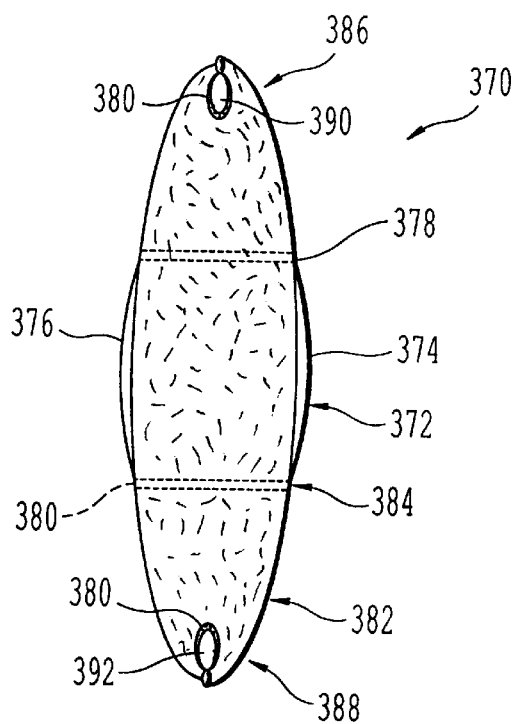
FIG. 33 is a side view of the IOL shown in FIG. 32.
Figure 34:
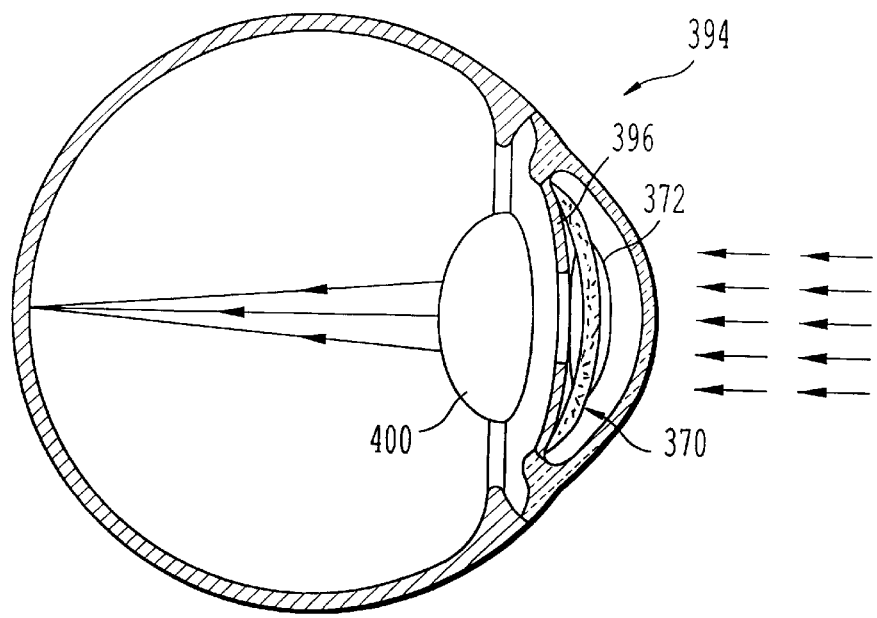
FIG. 34 is a cross-sectional view of an eye implanted with an IOL as shown in FIGS. 32 and 33.
Figure 35:
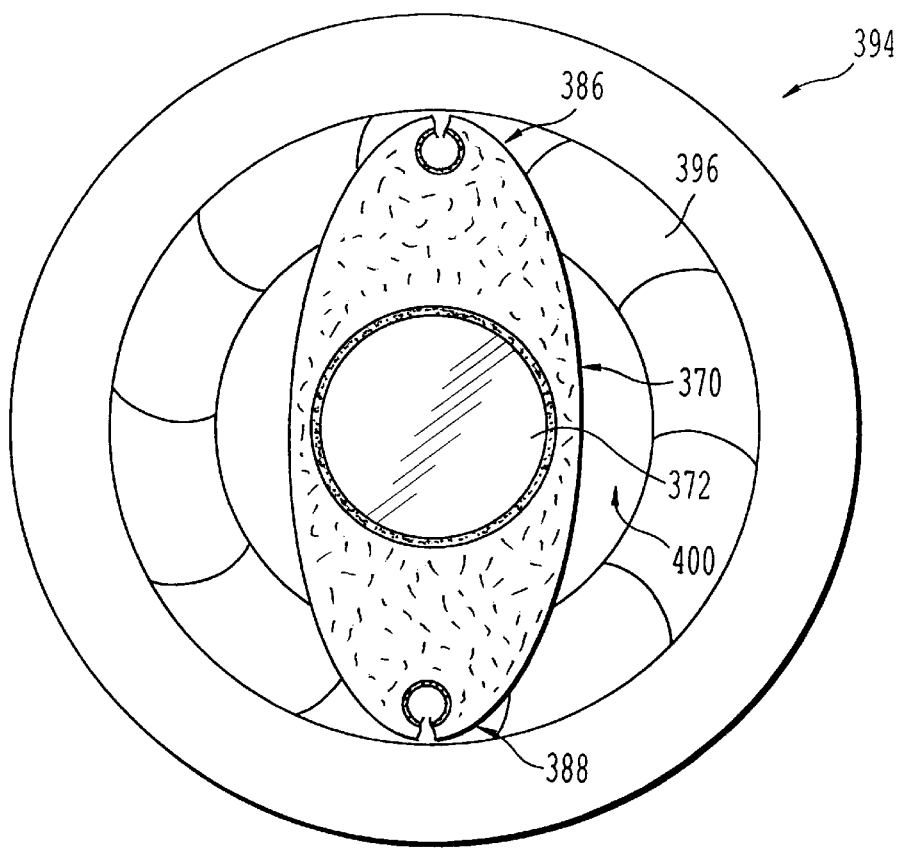
FIG. 35 is a front cross-sectional view of the eye and implanted IOL as shown in FIG. 34.
Figure 36:
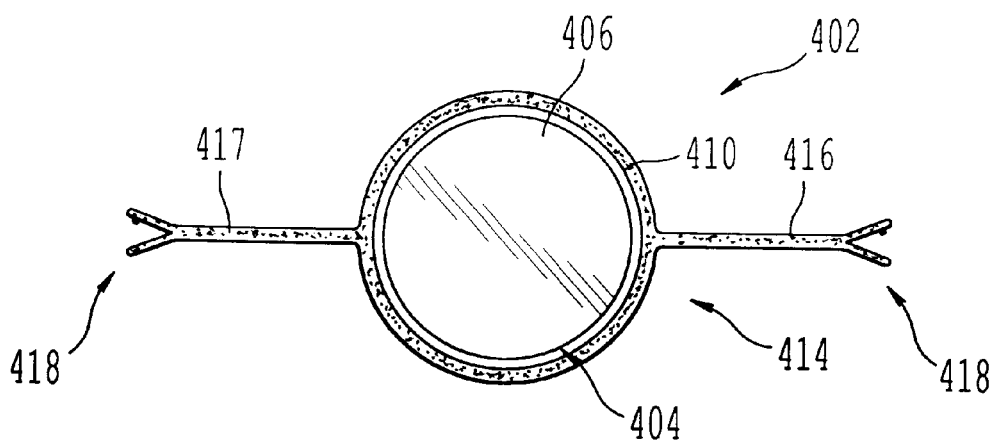
FIG. 36 is a front view of an IOL having another claw-type mounting structure according to a further embodiment of the present invention.
Figure 37:
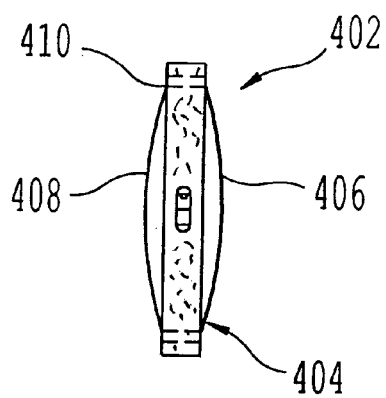
FIG. 37 is a side view of the IOL shown in FIG. 36.

Accordingly, as shown in FIGS. 32 and 33, the IOL 370 can be mounted in an eye 394 so that the claw portions 386 and 388 of lens mounting portion 382 attach to, for example, the iris 396 of the eye 394 to position the IOL 370 in the interior chamber 398 of the eye 394 as can be appreciated by one skilled in the art. The IOL 370 can be implanted in addition to the natural lens 400 of the eye 394, or in place of the natural lens 400 if the natural lens 400 has been removed. As in the IOLs and IOL systems described above, the light-absorbing material of the lens portion 372 and lens mounting portion 382 absorbs unwanted light eliminate glare and the halo effect perceived by the eye 394.

Another arrangement of the of an IOL for mounting the interior chamber of the eye is shown in FIGS. 36–39. As illustrated, IOL 402 includes include a lens portion 404 which, like the lens portions describe above, includes a first surface 406, a second surface 408 and a perimeter 410. The first and second 406 and 408 can have any suitable shape to provide the lens portion 404 with any suitable refractive power. Also, a light-absorbing material 412 similar to those described above is disposed on, in or proximate to the perimeter 410 to absorb unwanted light in the manner similar to that described above.

The IOL 402 further includes a lens mounting portion 414 comprising connecting arms 416 and 417. The lens mounting portion 414 and its connecting arms 416 and 417 are made of a flexible material, and include a light absorbing material similar to the those described above.

Figure 38:
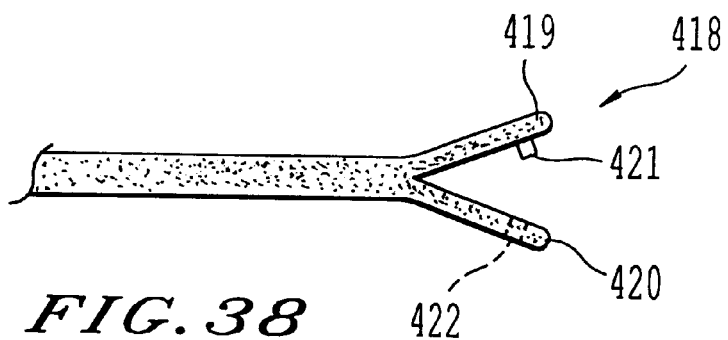
FIG. 38 is a detail view of the claw portions of the IOL shown in FIG. 36.

As shown in FIG. 38, each connecting arm 416 and 417 has a claw-portion 418, which has a forcep-like shape and includes arms 419 and 420. In this example, arm 419 includes a male portion 421, and arm 420 includes a female portion 422, such as an opening.

Figure 39:
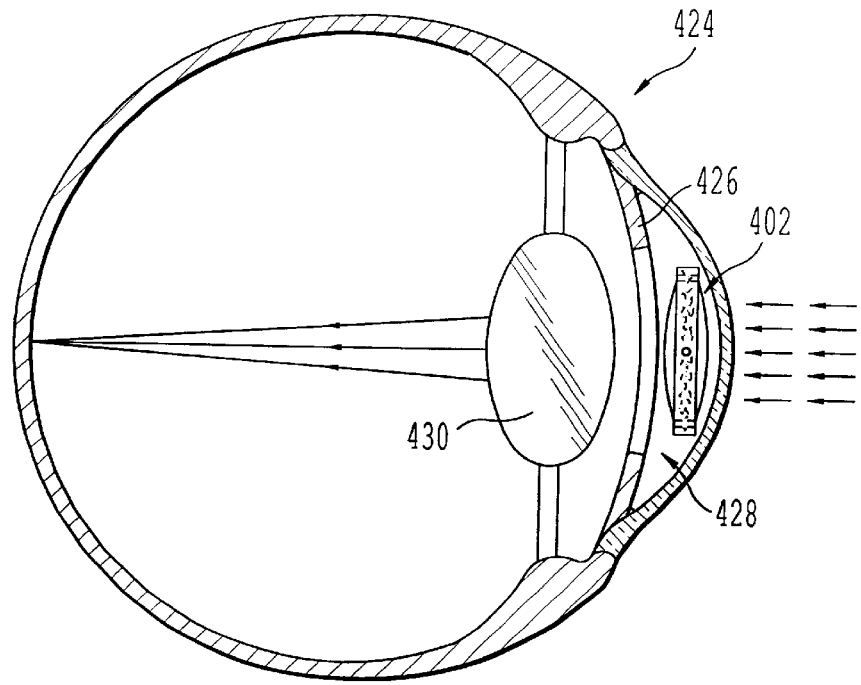
FIG. 39 is a cross-sectional view of an eye having the IOL shown in FIGS. 36 and 37 mounted therein.
Figure 40:
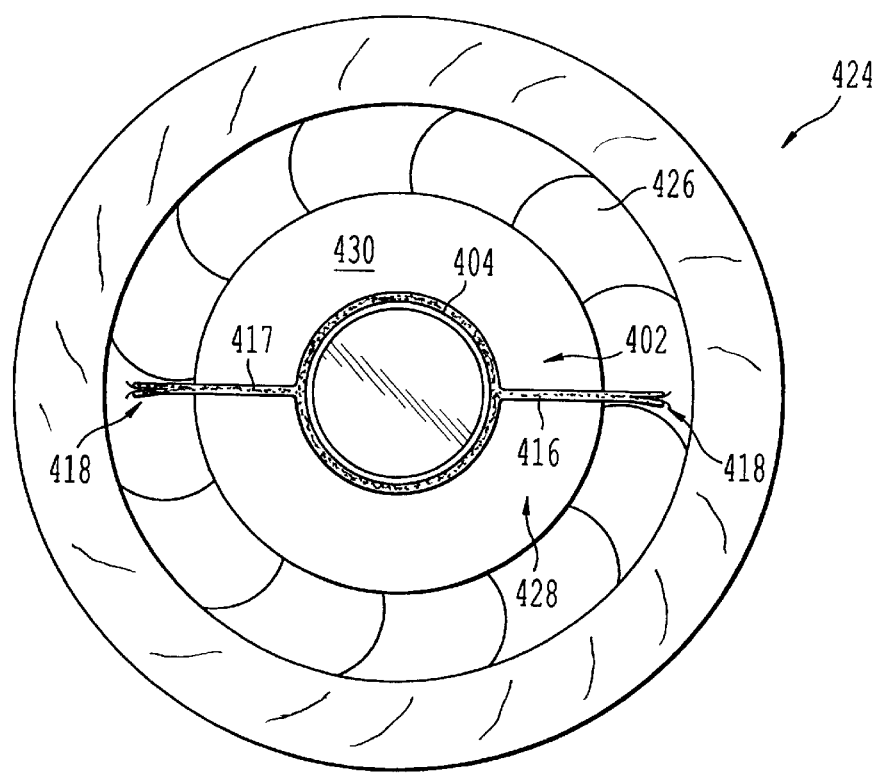
FIG. 40 is a front cross-sectional view of the eye an implanted IOL as shown in FIG. 38.

As shown in FIGS. 39 and 40, the connecting arms 416 and 417 of the lens mounting portion can attach to, for example, the inner portion of an eye 424 in front of the iris 426 which forms the anterior chamber 428 of the eye 424 as can be appreciated by one skilled in the art. Specifically, male portion 421 engages with female portion 422 to grip a portion of the inner portion of the eye 424 between arms 419 and 420. Accordingly, the IOL 402 can be implanted in the eye 424 in addition to the natural lens 430 of the eye 424, or in place of the natural lens 430 if the natural lens 430 has been removed. Also, the light-absorbing material of the lens portion 404 and lens mounting portion 414 absorbs unwanted light to eliminate glare and the halo effect experienced by eye 424.

As shown in FIGS. 41–44, the claw-type arrangement or IOL 440 for mounting in the anterior chamber of the eye can be modified to have holes or openings 442, 442-1 and 443 through the lens portion 444 or lens mounting portion 446. The openings allow aqueous fluid 448 to pass from behind the iris 396 through the IOL and into the anterior chamber 398. The fluid passing into the anterior chamber relieves intraocular pressure and may reduce the risk of glaucoma.

Figure 41:
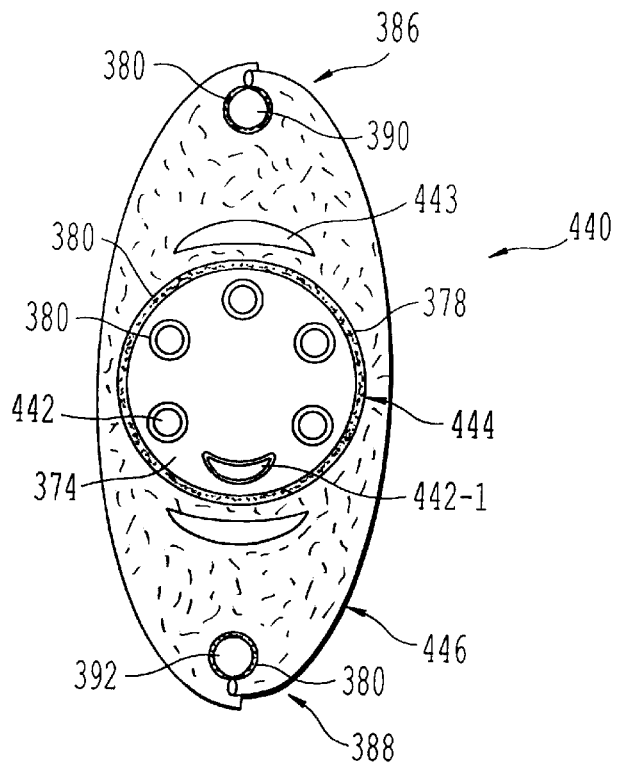
FIG. 41 is a front view of the IOL shown in FIG. 32 with openings cut into the lens and the claw-type attachment structure.
Figure 42:
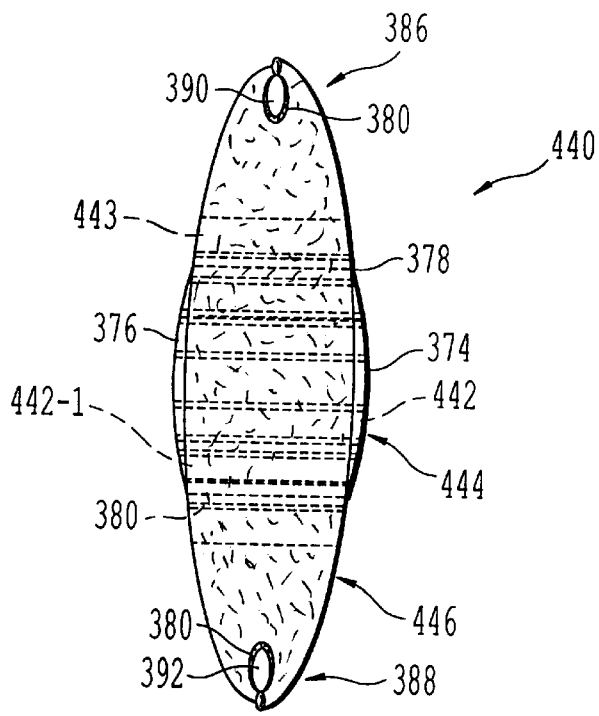
FIG. 42 is a side view of the IOL shown in FIG. 41.

Openings 442, 442-1 and 443 pass entirely through lens 444 and/or through lens mounting portion 446 and are preferably cylindrical or crescent shaped, as shown in FIG. 41. However, the openings may be any shape that allows aqueous fluid to pass from behind the iris and into the anterior chamber and may be located either in the lens itself or in the lens mounting portion itself, or any combination thereof. In addition, any number of openings may be present, including one opening located in the lens or lens mounting portion.

All other aspects of IOL 440 are substantially similar to IOL 370 shown in FIGS. 32–35, and the features of IOL 440, which are similar to IOL 370, are identified with like reference numbers. The same description of those similar features is applicable.

Figure 43:
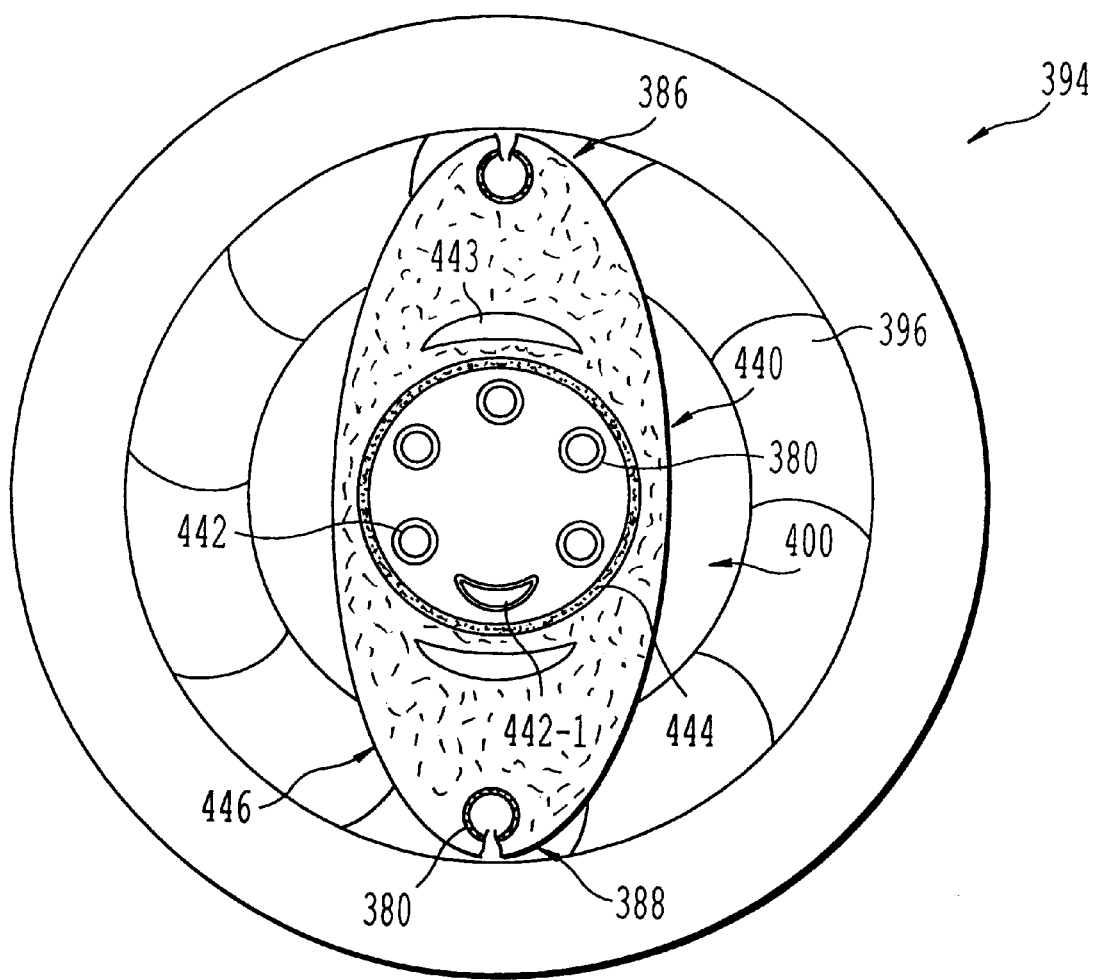
FIG. 43 is a front cross-sectional view of the eye and an implanted IOL shown in FIGS. 41 and 42.
Figure 44:
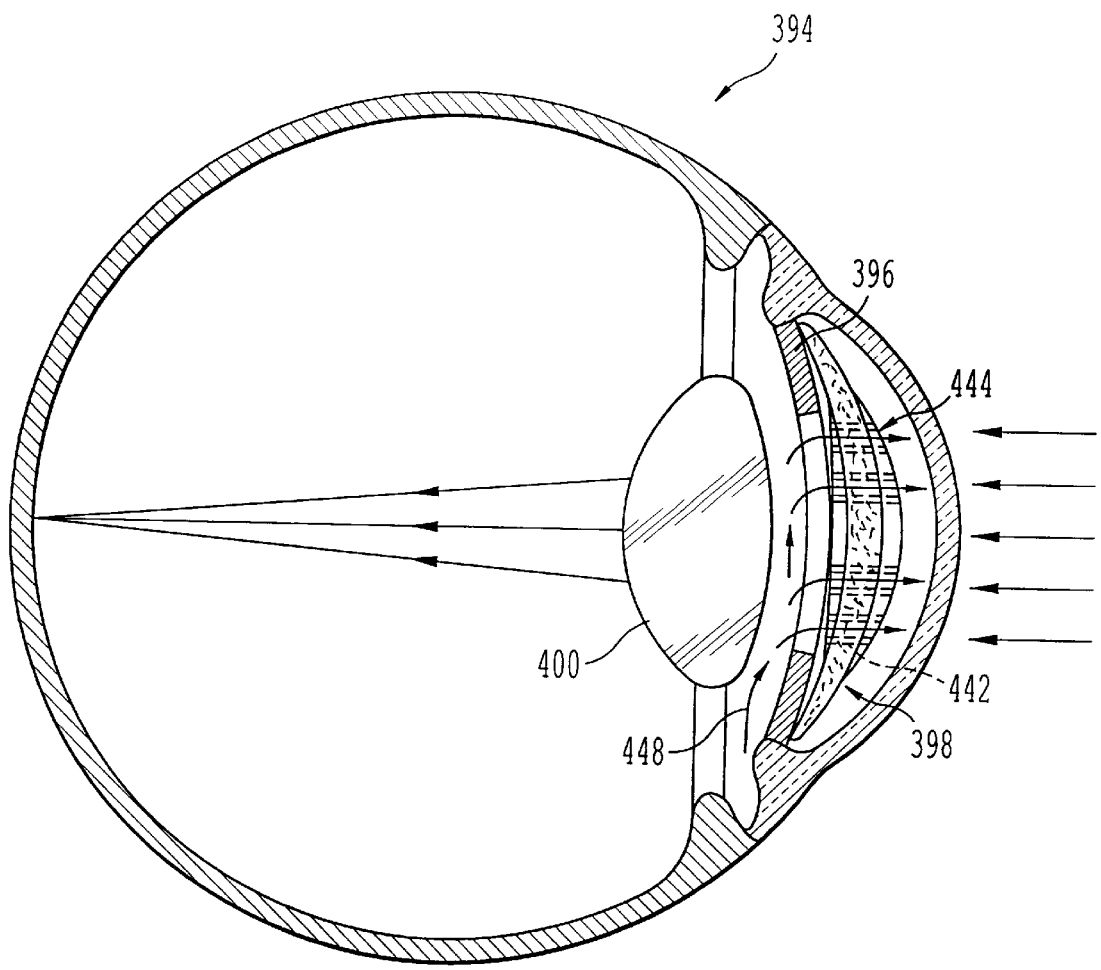
FIG. 44 is a cross-sectional view of an eye and an implanted IOL shown in FIGS. 41 and 42 with aqueous fluid flowing therethrough.

Accordingly, as shown in FIGS. 43 and 44, the IOL 440 can be mounted in eye 394 so that the claw portions 386 and 388 of lens mounting portion 446 attach to, for example, the iris 396 of the eye 394 to position the IOL 440 in the anterior chamber 398 of the eye 394 as can be appreciated by one skilled in the art. The IOL 440 can be implanted in addition to the natural lens 400 of the eye 394, or in place of the natural lens 400 if the natural lens 400 has been removed. Also, a light-absorbing material of the type described above can be placed in or at the surfaces forming openings 442, 442-1 and, if necessary, 443. As in the IOLs and IOL systems described above, the light-absorbing material 380 of the lens portion 372, lens mounting portion 382 and openings 442, 442-1 and 443 absorbs unwanted light eliminating glare and the halo effect perceived by the eye 394.

Figure 45:
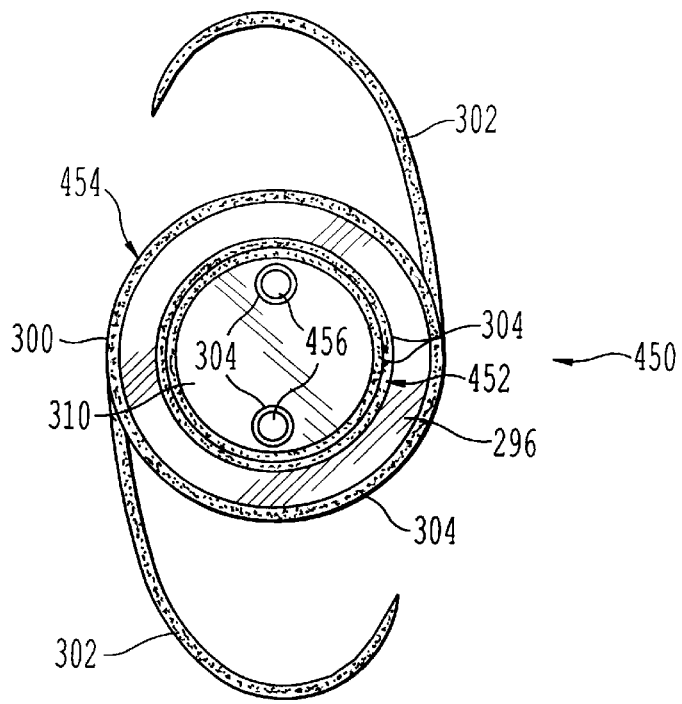
FIG. 45 is a front view of the IOL shown in FIGS. 21 and 22 with openings cut into the lens.
Figure 46:
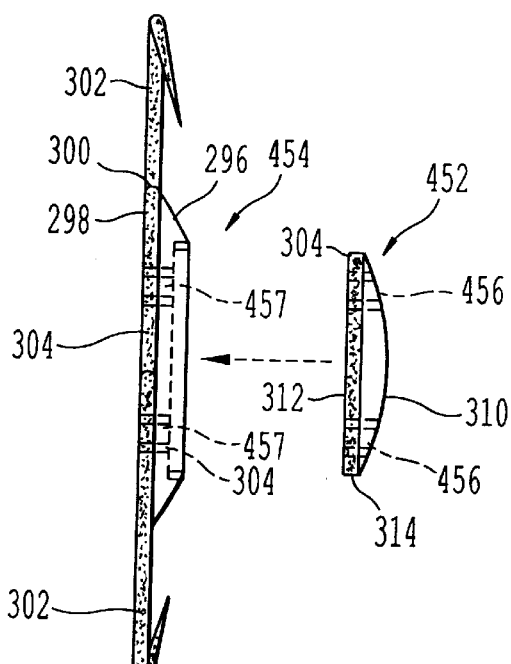
FIG. 46 is an exploded side view of the IOL shown in FIG. 45.

As shown in FIGS. 45 and 46, IOL 450 is piggyback lens system that can be configured so that the piggyback lens or front lens 452 interlocks with the rear lens 454. In addition, IOL 450 has openings 456 and 457 through piggyback lens 452 and the front lens 454, respectively, allowing aqueous fluid to pass therethrough as described above. The openings 456 and 457 are designed to align when piggyback lens 452 is coupled with rear lens 454 and form a continuous through passageway in the IOL 450.

IOL 450 may have one or more openings and the openings may be any shape that allows aqueous fluid to flow therethrough, as described above. IOL 450 is substantially similar to IOL 293, shown in FIGS. 21 and 22, and the features of IOL 450, which are similar to IOL 293, are identified with like reference numbers. The same description of those similar features and the use and placement of IOL 293 is applicable to IOL 450.

Accordingly the IOL 450 can be mounted in eye so that the haptics 302 attach to, for example, the iris of the eye to position the IOL 450 in the anterior chamber of the eye as can be appreciated by one skilled in the art. The IOL 450 can be implanted in addition to the natural lens of the eye, or in place of the natural lens if the natural lens has been removed. A light-absorbing material 304 of the type described above can be placed in or at the surfaces forming openings 456 and 457. As in the IOLs and IOL systems described above, the light-absorbing material 304 of the piggyback lens 452, rear lens 454 and iridectomies 456 and 457 absorbs unwanted light eliminate glare and the halo effect perceived by the eye.

Figure 47:
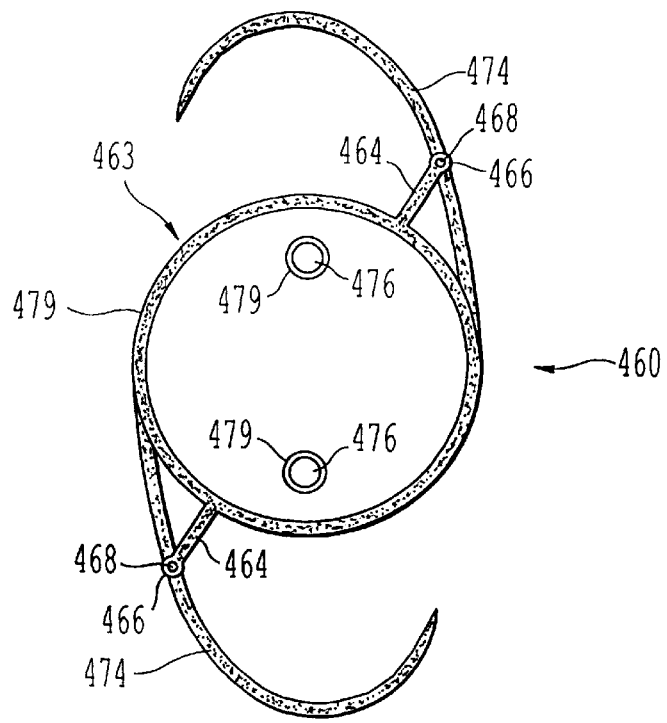
FIG. 47 is a front view of another piggyback IOL system according to a further embodiment of the present invention with openings cut into the lens.
Figure 48:
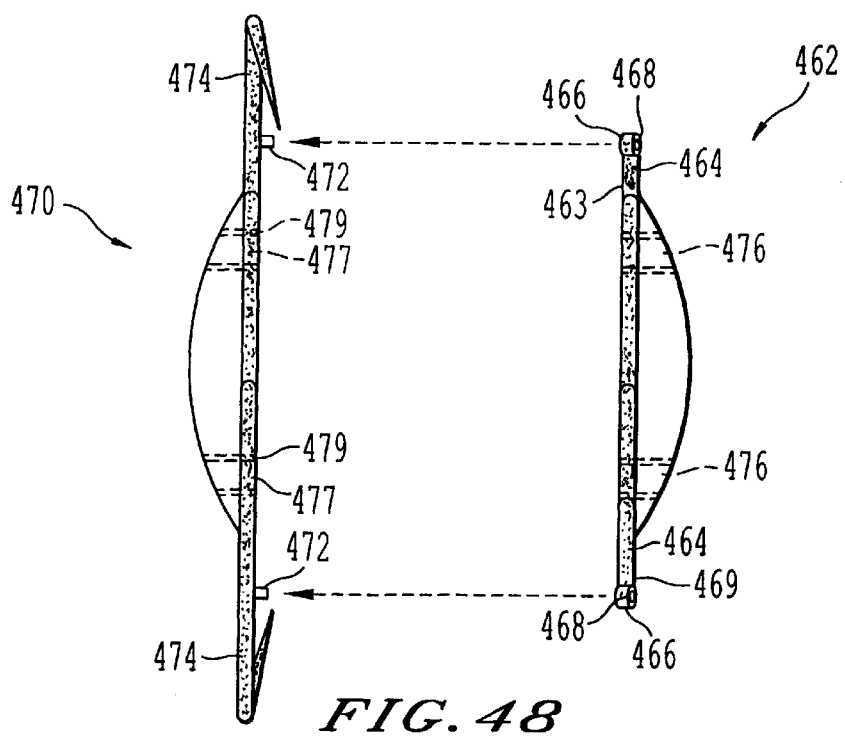
FIG. 48 is an exploded side view of the IOL shown in FIG. 47.

As shown in FIGS. 47 and 48, IOL 460 is another embodiment of a piggyback lens system. Piggyback lens 462 has a lens frame 463 with two arms 464 extending substantially perpendicular from the lens frame. The arms 464 have circular female members 466 with through passageways 468 attached at free ends 469 of arms 464.

The rear lens 470 has two cylindrical male members 472 fixedly attached to haptics 474. The male members are received within openings 468 of female members 466, coupling the piggyback lens to the rear lens. This piggyback system allows the piggyback lens to be easily changed with another lens at any time before or after implanting IOL 460 is an eye, enabling the IOL to compensate for changes in vision.

Additionally, IOL 460 has openings 476 and 477 that pass through both piggyback lens and the rear lens, respectively, allowing aqueous fluid to pass therethrough and reducing intraocular pressure. Openings 476 and 477 are substantially similar to those described above and may vary in shape and in number from one to as many may fit into the lenses without significantly effecting vision. The openings 476 and 477 are designed to align and form a continuous through passageway in the IOL 460.

A light absorbing material of the type described above can be placed in or at the surfaces forming the openings 426 and 427. As in the IOLs and IOL systems described above, a light-absorbing material 479 of the piggyback lens 462, the arms 464, the rear lens 470, the haptics 474, and the openings 476 and 477 absorb unwanted light and eliminate glare and the halo effect perceived by the eye.

Accordingly the IOL 460 can be mounted in eye so that the haptics 474 attach to, for example, the iris of the eye to position the IOL 460 in the anterior chamber of the eye as can be appreciated by one skilled in the art. The IOL 460 can be implanted in addition to the natural lens of the eye, or in place of the natural lens if the natural lens has been removed.

Figure 49:
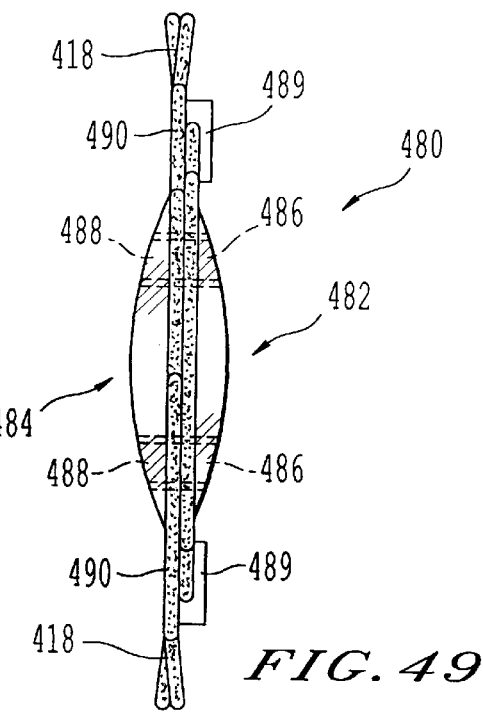
FIG. 49 is a side view of another piggyback IOL system according to a further embodiment of the present invention with an opening cut into the lens.
Figure 50:
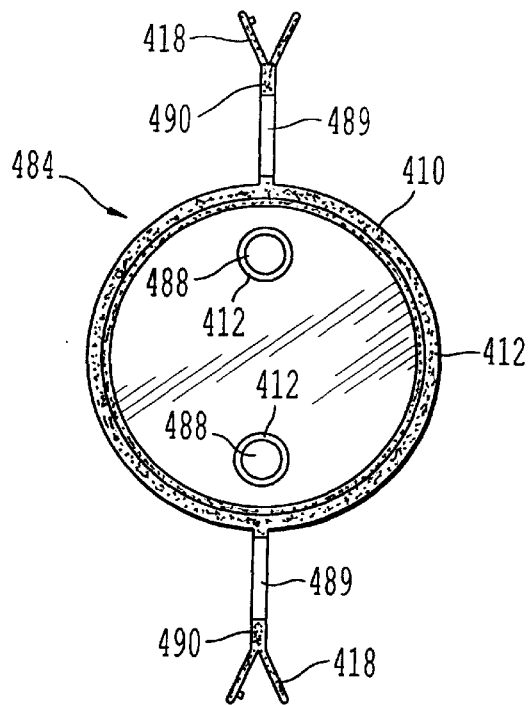
FIG. 50 is a front view of the rear lens of the IOL system shown in FIG. 49.

FIGS. 49–50 show another embodiment of a piggyback lens system. IOL 480 has a piggyback lens 482 and a rear lens 484. Piggyback lens 482 and rear lens 484 have openings 486 and 488, respectively passing through the lenses. Openings 486 are designed to align with openings 488 in the rear lens to form a continuous through passageway in the IOL 480 to allow passage of aqueous fluid. Openings 486 and 488 are substantially similar to those described above and may vary in shape and in number from one to as many may fit into the lenses without significantly effecting vision.

Additionally, lens 484 has substantially rectangular raised membranes 489 formed from silicon, plastic, polymethylmetracrylate, hydrogel, or any other suitable material extending perpendicular to the outer surface of arms 490. Membranes 489 do not necessarily have to rectangular and may be any size and shape desirable. Arms 490 are substantially similar in form and function as arms 416 and 417, shown in FIGS. 36–38. Raised membranes 489 allow piggyback lens 482 to couple to lens 484 by using claw-portions 492 on arms 494 to grip raised membranes 489. Arms 494 are substantially similar to arms 490, except that arms 494 are shorter, allowing claw-portions 492 to grip membranes 489 and securely couple the two lenses adjacent each other.

Rear lens 484 and piggyback lens 482 are substantially similar to lens 402, shown in FIGS. 36–40, and the features of IOL 480, which are similar to IOL 402, are identified with like reference numbers. The same description of those similar features and the use and placement of IOL 402 is applicable to IOL 480.

A light absorbing material of the type described above can be placed in or at the surfaces forming the openings 486 and 488. As in the IOLs and IOL systems described above, the light-absorbing material of the membrane 489, piggyback lens 482, the rear lens 484, the arms 490 and 494, the claw-portions 492, and the openings absorb unwanted light and eliminates glare and the halo effect perceived by the eye.

Accordingly the IOL 480 can be mounted in eye so that the claw-portions 418 attach to, for example, the iris of the eye to position the IOL 480 in the anterior chamber of the eye as can be appreciated by one skilled in the art. The IOL 480 can be implanted in addition to the natural lens of the eye, or in place of the natural lens if the natural lens has been removed.

Figure 52:
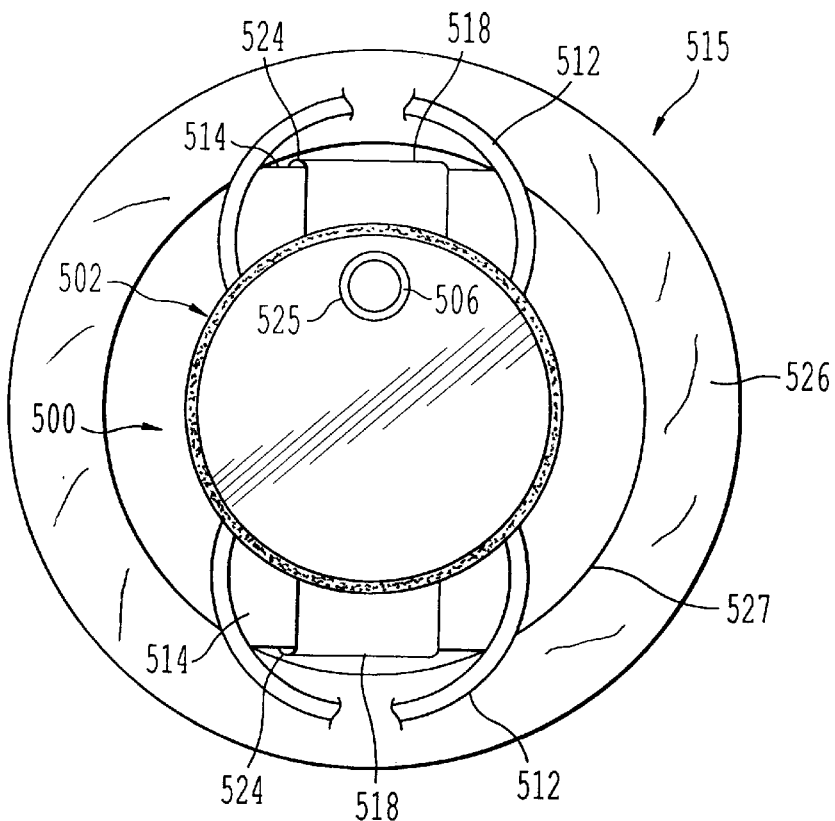
FIG. 52 is a front cross-sectional view of the eye and an implanted piggyback IOL system according to a further embodiment of the present invention with an opening cut into the lens.
Figure 53:
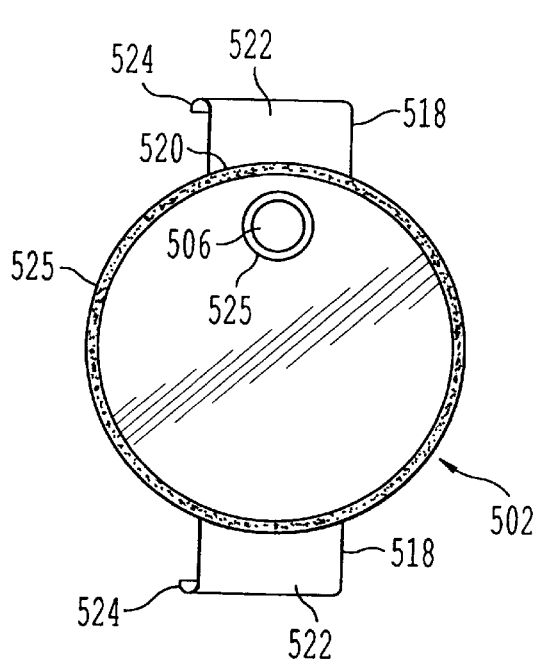
FIG. 53 is a front view of the front lens of the IOL system shown in FIG. 52.
Figure 54:
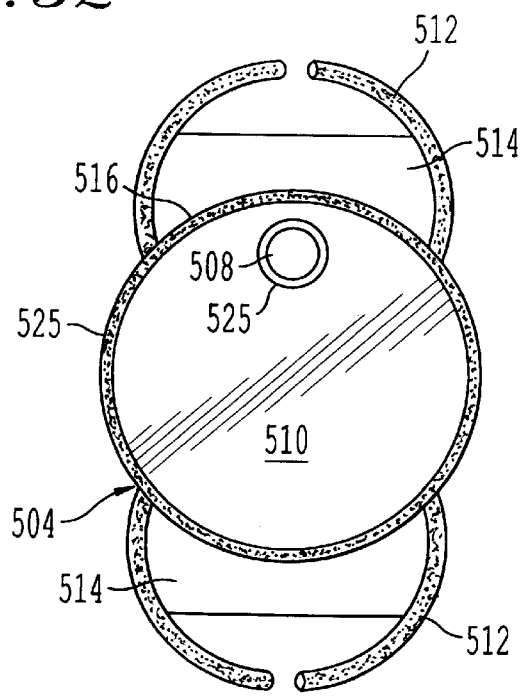
FIG. 54 is a front view of the rear lens of the IOL system shown in FIG. 52.
Figure 55:
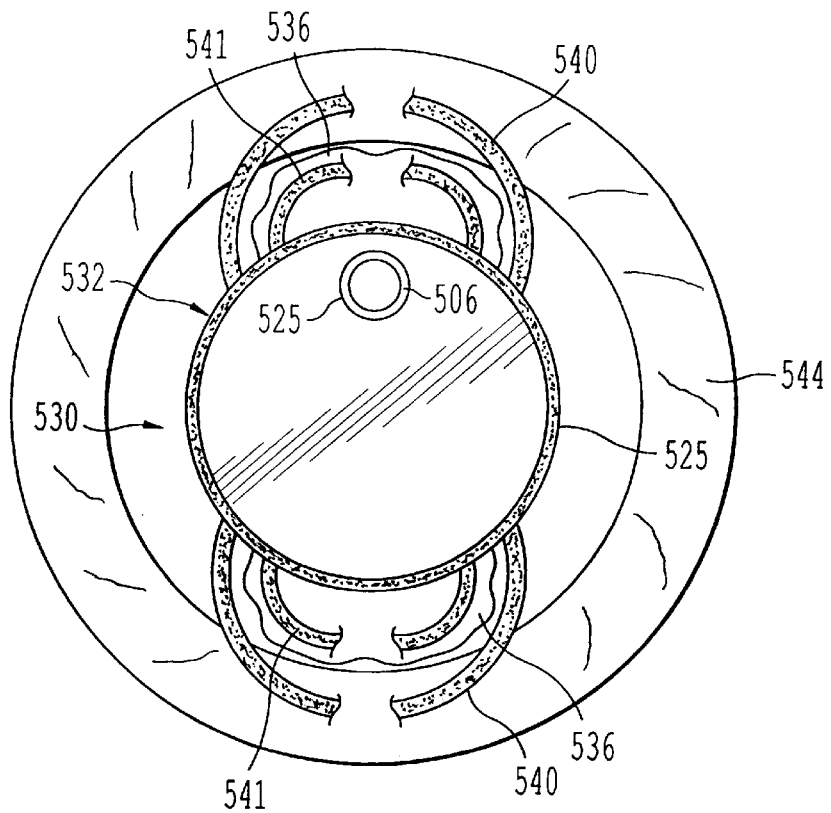
FIG. 55 is a front cross-sectional view of the eye and an implanted piggyback IOL system according to a further embodiment of the present invention with an opening cut into the lens.
Figure 56:
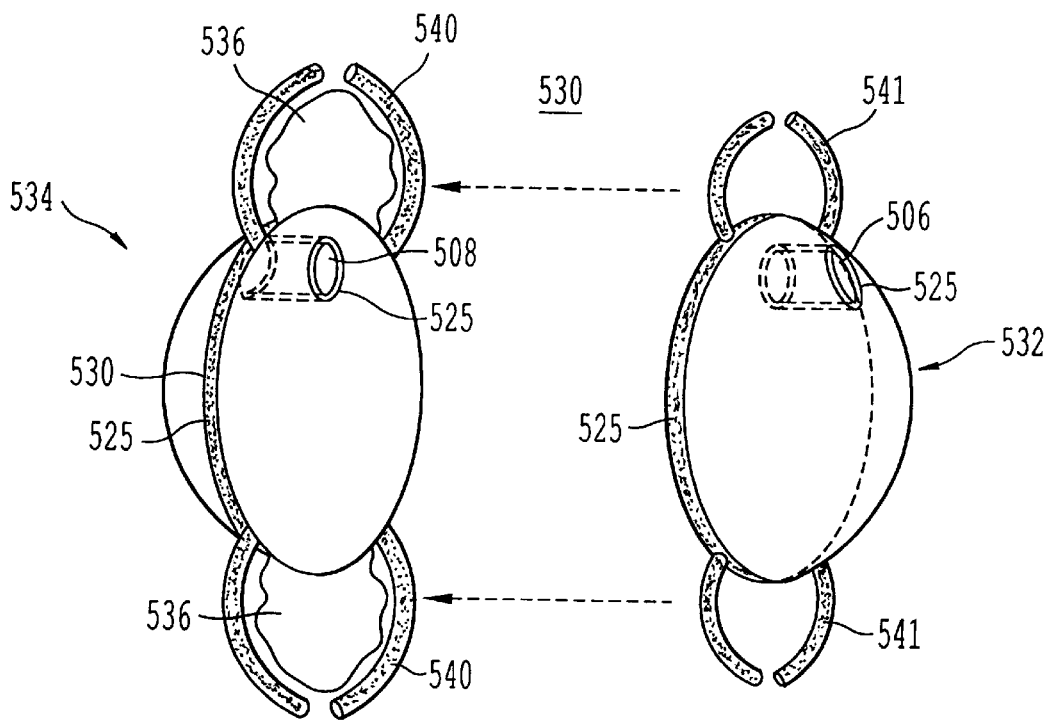
FIG. 56 is an exploded perspective side view of the IOL system shown in FIG. 55.
Figure 57:
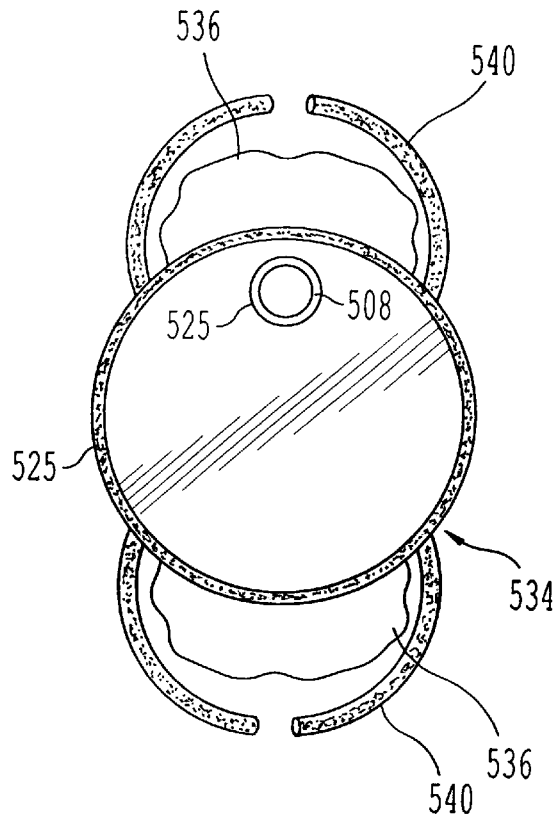
FIG. 57 is a front view of the rear lens of the IOL system shown in FIG. 56.
Figure 58:
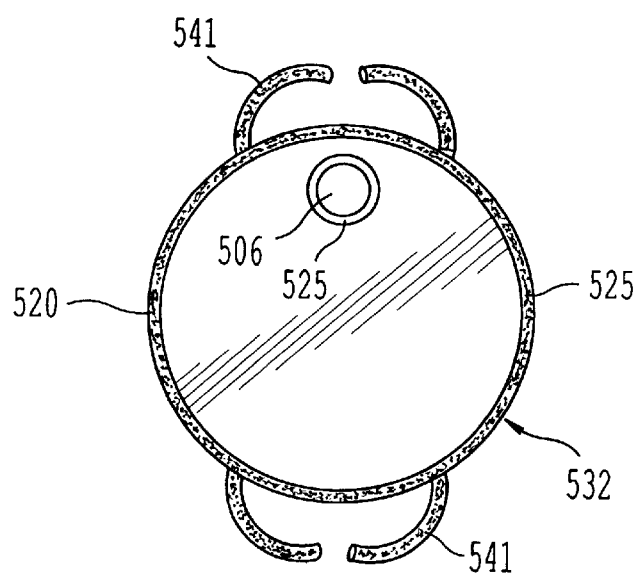
FIG. 58 is a front view of the front lens of the IOL system shown in FIG. 56.

As seen in FIGS. 52–54, IOL 500 is another piggyback lens systems. IOL has piggyback lens 502 and rear lens 504. Piggyback lens 502 and rear lens 504 have openings 506 and 508, respectively passing through the lenses. Openings 506 are designed to align with openings 508 in the rear lens to form a continuous through passageway in the IOL 500, allowing passage of aqueous fluid therethrough. Openings 506 and 508 are substantially similar to those described above and may vary in shape and in number from one to as many may fit into the lenses without significantly effecting vision.

Lens portion 510 of rear lens 504 is substantially similar to lens portion 112 of IOL 110, shown in FIGS. 3 and 4. However, rear lens 504 has claw-portions 512 formed of surgical steel or any other suitable non-biodegradable material. In this example, the claw-portions of rear lens 504 attach to the iris 526 to mount the IOL 500 in the eye 515, as seen in FIG. 52. Additionally, rear lens 504 has membranes 514 formed of silicon, plastic, polymethylmetracrylate, hydrogel, or any other suitable material extending between each claw on claw-portions 512 and vertically away from the outer edge 516 of lens portion 510.

Piggyback lens 502 is substantially similar to the lens described above, however, piggyback lens 502 has hooks 518 formed of surgical steel or any other suitable non-biodegradable material, extending perpendicularly from edge 520 of lens 502 and are fixedly attached to the lens. Hooks 518 have a planar surface 522 that is generally rectangular and have U-shaped portions 524 that allow hooks 518 to releasably attach to membranes 514 of rear lens 504, as shown in FIG. 52. IOL 500 will also eliminate glare and the halo effect due to the presence of light-absorbing material 525 in or at the edges 516 and 520, at the claw-portions 512, the hooks 518, at the surfaces forming the openings 506 and 508 and at the membrane 514.

Accordingly, as shown in FIG. 52, the IOL 500 can be mounted in eye so that the claw portions 512 of rear lens 504 attach to, for example, the iris 526 of the eye 515 to position the IOL 500 in the anterior chamber of the eye as can be appreciated by one skilled in the art. The IOL 500 can be implanted in addition to the natural lens 527 of the eye, or in place of the natural lens if the natural lens has been removed.

As shown in FIGS. 55–58, piggyback lend system or IOL 530 is similar to piggyback IOL 500, shown if FIGS. 52–54. Rear lens 534 is substantially similar to rear lens 504. The only difference being the membranes 536 of rear lens 534. In rear lens 504, the membranes extend between and are attached to claw portions 512; however, in rear lens 534, membranes 536 extends away from edge 538 and in between claw-portions 540, but is not attached to the claw-portions. All other aspects of rear lens 534 are substantially similar to rear lens 504 shown in FIG. 54, and the features of rear lens 534, which are similar to rear lens 504, are identified with like reference numbers. The same description of those similar features is applicable.

The piggyback lens 532 is designed to operate in a similar fashion to rear lenses 504 and 534. Lens 532 has claw-portions 541 that extend from edge 542 and attach to membranes 536 in a similar fashion as that in which claw-portions 540 attach to the iris 544.

In all other respects, IOL 530 is substantially similar to IOL 500 and the features of IOL 530, which are similar to IOL 500, are identified with like reference numbers. The same description of those similar features and the use and placement of IOL 500 is applicable to IOL 530.

Accordingly IOL 530 can be mounted in eye so that the claw-portions 540 attach to, for example, the iris of the eye to position the IOL 530 in the anterior chamber of the eye as can be appreciated by one skilled in the art. The IOL 530 can be implanted in addition to the natural lens of the eye, or in place of the natural lens if the natural lens has been removed. A light-absorbing material of the type described above can be placed in or at the surfaces forming openings 506 and 508. As in the IOLs and IOL systems described above, the light-absorbing material 525 of the piggyback lens 532 and rear lens 534 absorbs unwanted light eliminate glare and the halo effect perceived by the eye.

Figure 51:
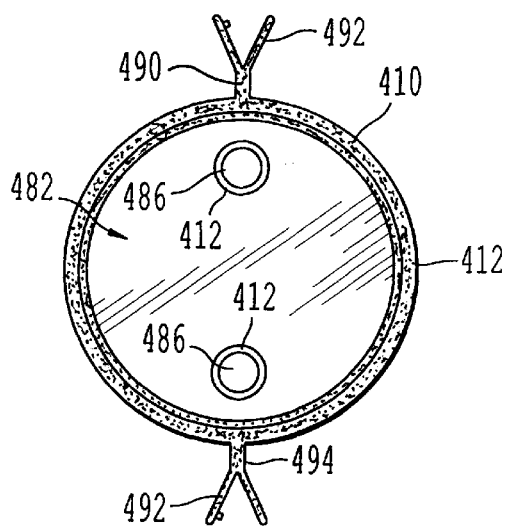
FIG. 51 is a front view of the front lens of the IOL system shown in FIG. 50.
Figure 59:
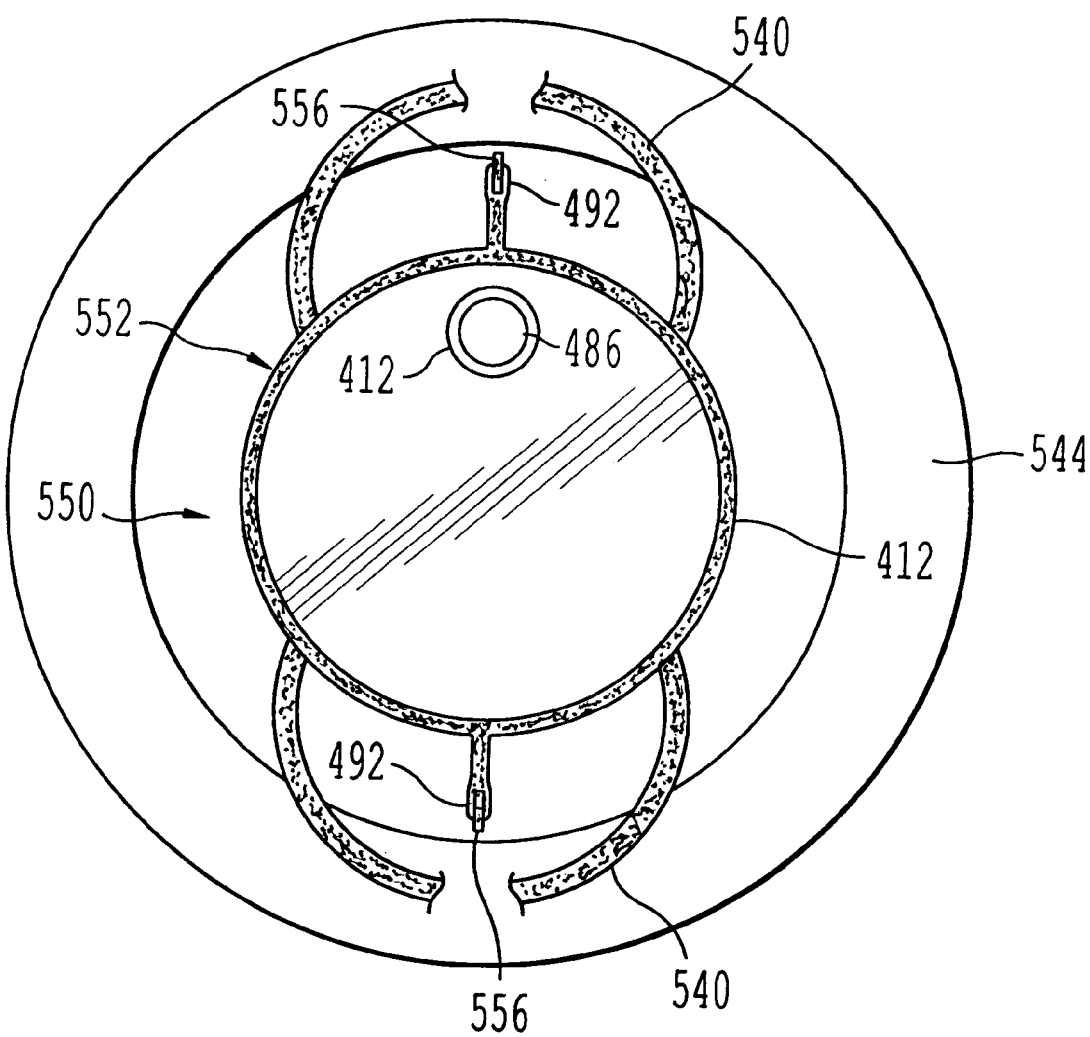
FIG. 59 is a front cross-sectional view of the eye and an implanted piggyback IOL system according to a further embodiment of the present invention with an opening cut into the lens.

FIGS. 59–61, show another embodiment of a piggyback lens system or IOL 550. In IOL 550, piggyback lens 552 is substantially similar to and has the same features and function as described above for piggyback lens 482, shown in FIGS. 49 and 51. In addition, rear lens 554 is a combination of rear lenses 484 and 534. Lens 554 is designed to operate in a similar fashion to rear lens 534. Lens 534 has claw-portions 540 that extend from edge 542 and attach to the iris 544. However, unlike lens 534, lens 554 has membranes 556 that extend away from edge 542 of the rear lens 554 and from first side 560 of rear lens 554 towards second side 562. In addition, the membranes have protrusions 564 at the distal ends 566 that allow claw-portions 492 to releasably attach to the membranes and couple piggyback lens 552 to rear lens 554.

Piggyback lens 552 is substantially similar to piggyback lens 482 and the features of lens 552, which are similar to piggyback lens 482 are identified with like reference numbers. The same description of those similar features and the use and placement of lens 482 is applicable to lens 552.

In all other respects, IOL 550 is substantially similar to IOL 530 and the features of IOL 550, which are similar to IOL 530, are identified with like reference numbers. The same description of those similar features and the use and placement of IOL 530 is applicable to IOL 550.

Accordingly the IOL 550 can be mounted in eye so that the claw-portions 540 attach to, for example, the iris of the eye to position the IOL 550 in the anterior chamber of the eye as can be appreciated by one skilled in the art. The IOL 550 can be implanted in addition to the natural lens of the eye, or in place of the natural lens if the natural lens has been removed. A light-absorbing material of the type described above can placed in or at the surfaces forming openings 486 and 508. As in the IOLs and IOL systems described above, the light-absorbing material 412 of the piggyback lens 552 and rear lens 554 absorbs unwanted light eliminate glare and the halo effect perceived by the eye.

Figure 62:
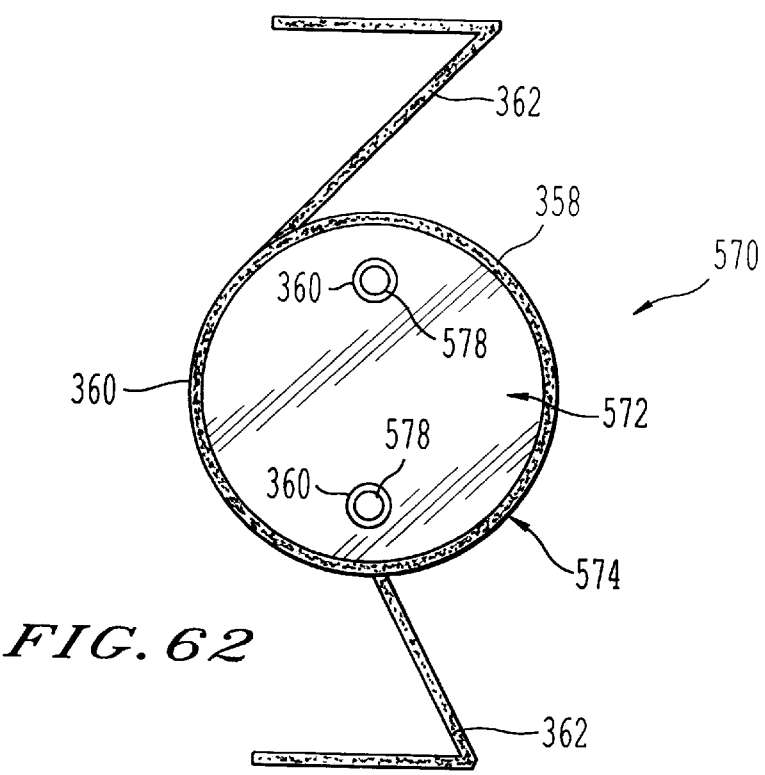
FIG. 62 is a front view of the IOL system shown in FIG. 17 with opening cut into the lens.
Figure 63:
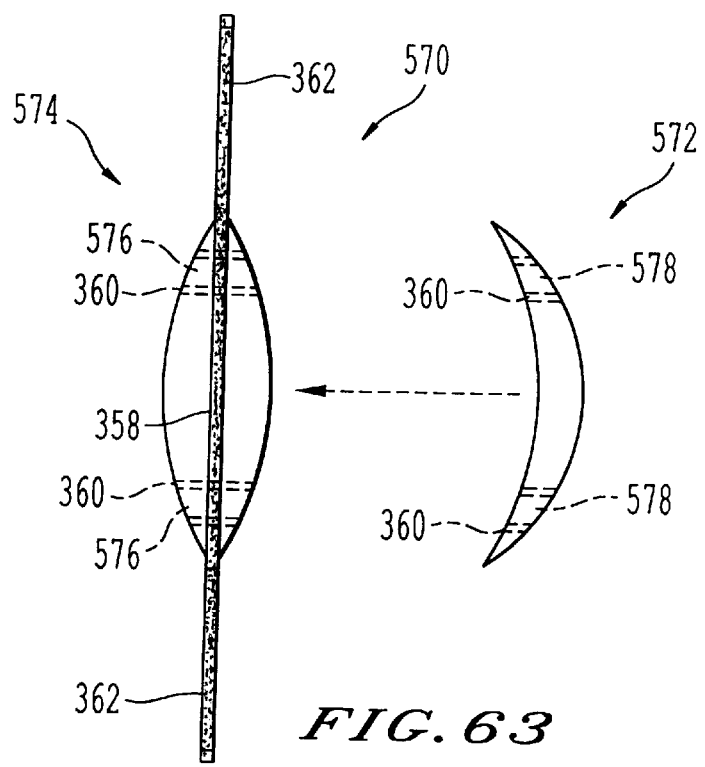
FIG. 63 is an exploded side view of the IOL system shown in FIG. 62.

FIGS. 62 and 63 show another piggyback lens system or IOL 570. IOL 570 has a rear lens 574 that is generally similar to lens portion 352 and haptic arrangement 362 of IOL 350. However, lens 574 has openings 576 that are designed to align with openings 578 in piggyback lens 572 and form a continuous through passageway in the IOL 550, as seen in FIG. 63. This passageway allows aqueous fluid to pass from behind the iris through the IOL 550 and into the anterior chamber, relieving intraocular pressure.

Piggyback lens 572 allows changing of the refractive power of IOL 550 without completely removing the IOL. After simultaneous implantation of both the piggyback lens 572 and the rear lens 574, it may be necessary to change the refractive power of the IOL if the refractive power is incorrect. A small incision can be made in the eye, enabling only the piggyback lens to be removed and replaced with another lens having the proper refractive power. Piggyback back lens 572 may be coupled to the rear lens in any fashion that allows easy separation between the two lenses. Preferably, the two lenses are coupled together using the piggyback embodiments disclosed above. This type of IOL creates two optics out of one.

Furthermore, piggyback lens 572, rear lens 574, or both, can be concave, convex, planar, or have any other suitable shape or types of shapes for complementing or replacing the natural lens of the eye and, if necessary, for correcting the vision disorder of the eye as appropriate.

Accordingly the IOL 570 can be mounted in the eye so that the haptics hold the IOL 570 in the anterior chamber of the eye as can be appreciated by one skilled in the art. The IOL 570 can be implanted in addition to the natural lens of the eye, or in place of the natural lens if the natural lens has been removed. A light-absorbing material as described above can be placed in or at the surfaces forming the openings 576 and 578. As in the IOLs and IOL systems described above, the light-absorbing material 525 of the piggyback lens 572, rear lens 574, the haptics 362 and the openings absorb unwanted light eliminate glare and the halo effect perceived by the eye.

Figure 64:
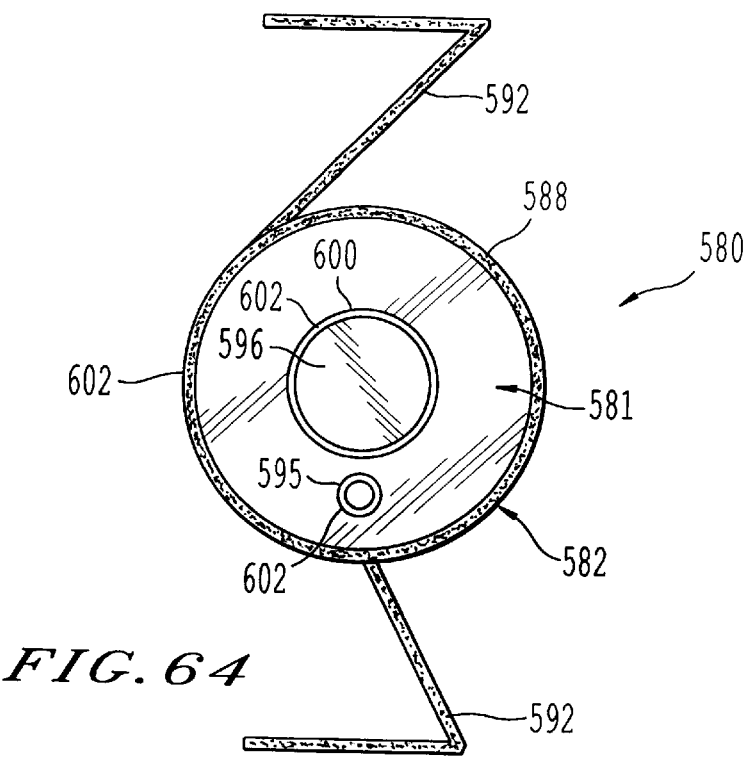
FIG. 64 is a front view of another piggyback IOL system according to a further embodiment of the present invention with an opening cut into the lens.
Figure 65:
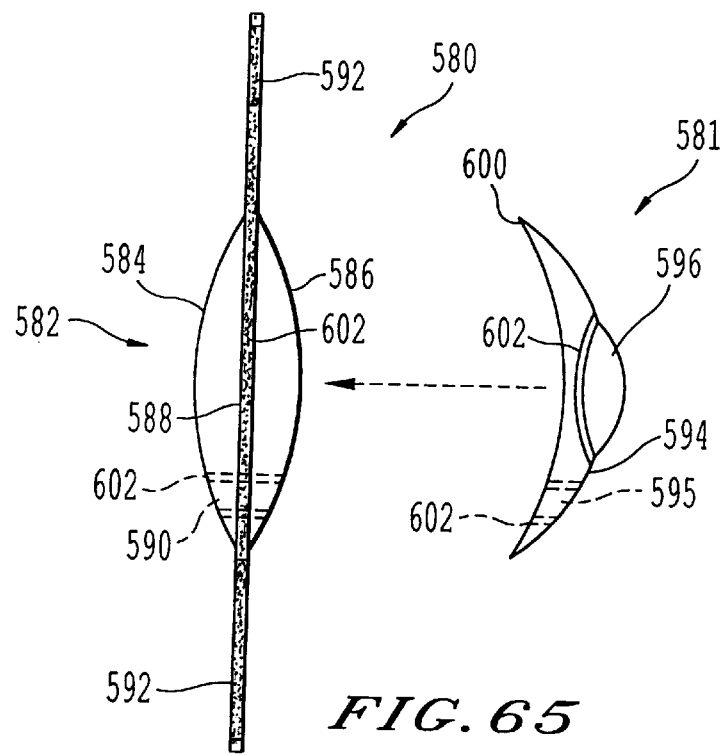
FIG. 65 is an exploded side view of the IOL system shown in FIG. 63.

As shown in FIGS. 64 and 65, an intraocular lens 580 according to this embodiment includes a piggyback lens 581, rear lens 582 having a first surface 584, a second surface 586, a perimeter 588 connecting the first and second surfaces and an opening 590. The rear lens 582 is generally similar in all respects to rear lens 557 described above, and can be mounted into eye in a manner similar to the IOLs described above. The IOL 580 also includes haptics 592 similar to those described above for IOL 350.

However, unlike the IOLs described above, piggyback lens 581 has first and second refractive portions 594 and 596 having first and second respective refractive powers.

A light-absorbing material 602 is disposed on or at the perimeters 588 and 600 of rear lens 582 and piggyback lens 581. This light-absorbing material 602 can be similar to light-absorbing material described above, and can be applied as a layer onto perimeters 588 and 600 impregnated into perimeters 588 and 600, or impregnating into rear and piggyback lenses 582 and 581 along perimeters 588 and 600 at a distance from perimeters 588 and 600.

In addition, the light-absorbing material 602 is disposed at the interface between first refractive portion 594 and second refractive portion 596 as illustrated. In this example, the light-absorbing material 602 can be applied at the interface between first refractive portion 594 and second refractive portion 596, or can be impregnated into piggyback lens 581 at that interface. Accordingly, the light-absorbing material 602 at the perimeters 588 and 600, the interface between the first refractive lens and the second refractive lens, and the openings absorb light propagating toward the perimeters 588 and 600, as well as light scattered in the rear and piggyback lenses 582 and 581 towards the perimeters 588 and 600. The light-absorbing material on the haptics 592 absorbs light impinging on the haptics so that the haptics 592 do not reflect that light. Accordingly, the light-absorbing material 602 prevents the eye into which IOL 580 is mounted from experiencing glare and the halo effect due to the presence of the IOL 580.

Accordingly the IOL 580 can be mounted in eye so that the haptics hold the IOL 580 in the anterior chamber of the eye as can be appreciated by one skilled in the art. The IOL 580 can be implanted in addition to the natural lens of the eye, or in place of the natural lens if the natural lens has been removed. As in the IOLs and IOL systems described above, the light-absorbing material 602 of the piggyback lens 581, rear lens 582, and the haptics 592 absorbs unwanted light eliminate glare and the halo effect perceived by the eye. In addition, the light-absorbing material can placed in or at the edges of openings 590 and 595.

Figure 66:
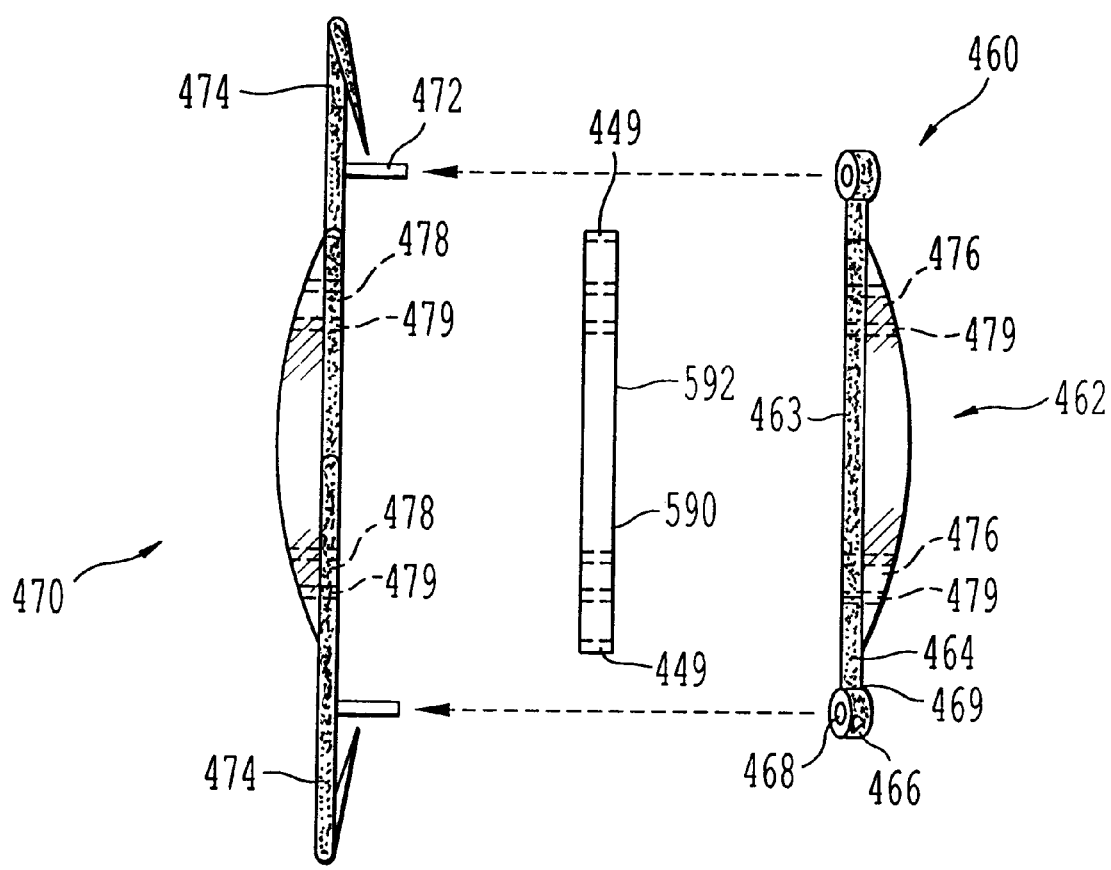
FIG. 66 is an exploded side view of the IOL system shown in FIGS. 47 and 48 with a clear plate inserted in between the two lenses.

As seen in FIG. 66, a thin transparent plate 590 may be inserted in between the piggyback lens and the rear lens of an IOL, such as IOL 460, shown in FIGS. 47 and 48. However, transparent plate 590 may be placed in between any of the piggyback lens system disclosed above or any other two-lens IOL systems. Transparent plate 590 may be made of a synthetic material such as silicone, polymethylmethacrylate, hydrogel, polysulfone, glass, or any other suitable material, can have an outer diameter of, for example, about 1 mm to about 12 mm, or any other suitable diameter, and can be circular, square, rectangular or any other suitable shape. Furthermore, first side 592 and second side 594 can be concave, convex, planar, or have any other suitable shape or types of shapes that results in the desired effect.

Openings 596 pass through plate 590 and align with openings 476 and 478 in piggyback lens 462 and rear lens 470, allowing aqueous fluid to pass therethrough. In addition, light absorbing material 479 is placed around openings 596 and the edge of plate 590 in the same manner as described above, absorbing unwanted light and eliminating glare and the halo effect perceived by the eye. Plate 590 may be inserted post operatively moving the piggyback lens forward and changing the focal point of the lens. The plate may be of any thickness that achieves the desired focal point.

Although few exemplary embodiments of this invention have been described in detail above, those skilled in the art will readily appreciate that many modifications are possible in the exemplary embodiments without materially departing from the novel teaching and advantages of this invention. Accordingly, all sorts of modifications are intended to be included within the scope of this invention at defining the following claims.

What is claimed is:

1. An intraocular lens, adapted for implantation into an eye to adjust a refractive power of an eye, comprising:
    a lens portion having first and second surfaces and a perimeter connecting said first and second surfaces and extending entirely about said lens portion;
    a plurality of third surfaces, each extending transversely to said first and second surfaces and defming a respective opening in said lens portion, each said opening being configured to allow aqueous fluid to pass therethrough; and
    a light absorbing material, disposed to absorb light propagating in a direction toward at least one of said perimeter and said third surfaces.

2. An intraocular lens as claimed in claim 1, wherein:
    said lens includes a lens mounting portion, adapted to secure the lens portion therein and being adapted to couple said lens portion to an interior portion of the eye.

3. An intraocular lens as claimed in claim 2, wherein:
    said lens mounting portion has at least one opening therein, adapted to allow aqueous fluid to pass therethrough.

4. An intraocular lens as claimed in claim 1, wherein:
    said light absorbing material is disposed at least one of said third surfaces.

5. An intraocular lens as claimed in claim 1, wherein:
    said light absorbing material is disposed at said perimeter.

6. An intraocular lens as claimed in claim 1, wherein:
    said lens includes at least one haptic, adapted to attach to a portion of the eye when said lens is implanted in the eye, said at least one haptic including a light absorbing material.

7. An intraocular lens system, adapted for implantation into an eye to adjust a refractive power of an eye, comprising:
    a first lens having first and second surfaces, and a first perimeter connecting said first and second surfaces and extending entirely about said first lens, said first lens futher having a first plurality of first openings therein, which are each configured to allow aqueous fluid to pass therethrough;
    a second lens having third and fourth surfaces and a second perimeter connecting said third and fourth surfaces and extending entirely about said second lens, said second lens further having a second plurality of second openings therein, which are each configured to allow aqueous fluid to pass therethrough; and
    a light absorbing material disposed to absorb light propagating in direction toward at least one of said perimeters and a direction toward any surfaces of said lens forming any of said openings.

8. An intraocular lens system as claimed in claim 7, wherein:
    said third surface is adapted to face said first surface of said first lens when said lens system is implanted into the eye.

9. An intraocular lens system as claimed in claim 7, wherein:
    said second lens is adapted to interlockingly couple to said first lens.

10. An intraocular lens system as claimed in claim 7, wherein:
    said first and second plurality or openings substantially align to define a through passageway extending entirely though said lens system.

11. An intraocular lens system as claimed in claim 7, wherein:
    said first and second plurality of openings have a light absorbing material disposed thereon.

12. An intraocular lens system as claimed in claim 7, further comprising:
    a third lens adapted for insertion between said first and second lenses.

13. An intraocular lens system as claimed in claim 7, wherein:
    at least one of said first and second lenses includes at least one haptic, said at least one haptic including a light absorbing material.

14. A method for using an intraocular lens system to adjust a refractive power of an eye, the intraocular lens system comprising a first lens having a first plurality of openings passing therethrough, the method comprising the steps of:
    inserting said intraocular lens system into said eye; and
    positioning said intraocular lens system such that said first plurality of openings are disposed to allow aqueous fluid to pass therethrough between the anterior chamber of the eye and the posterior chamber of the eye.

15. A method according to claim 14, wherein:
    said lens system further comprises a second lens having a second plurality of openings passing therethrough; and
    the inserting step includes the step of inserting the second lens into the eye.

16. A method according to claim 15, wherein said positioning step includes the step of:

positioning said second lens so that said second plurality of openings is substantially aligned with said first plurality of openings, forming a plurality of continuous passages through said first and second lenses for allowing aqueous fluid to pass therethrough.

17. A method according to claim 16, wherein:

at least one of said first and second lenses include a light absorbing material disposed; and said positioning step includes positioning the lens such that said light absorbing material is disposed to absorb at least some light propagating in a direction substantially radially of at least one of said first and second lenses.

18. A method according to claim 15, wherein:

at least one surface of said first and second lenses defining at least one of said first and second plurality of openings includes a light absorbing material; and said positioning step includes the step of positioning the lens such that said light absorbing material is disposed to absorb light propagating substantially radially of at least one of said first and second lenses.

* * * * *